(12) United States Patent
Reshef et al.

(10) Patent No.: US 12,168,092 B2
(45) Date of Patent: Dec. 17, 2024

(54) REPLACEABLE FLOW TRACT FOR AN INHALER

(71) Applicant: Syqe Medical Ltd., Tel-Aviv (IL)

(72) Inventors: Nimrod Reshef, LeHavim (IL); Itay Kurgan, Tel-Aviv (IL); Avishay Denizel, Holon (IL); Geva Rosenthal Kaplan, Ramat-Gan (IL); Roee Lifshitz, Moshav Beit Hillel (IL); Abraham Meyer, Tel-Aviv (IL); Binyamin Schwartz, Sde Eliezer (IL); Aaron Schorr, Lotem (IL)

(73) Assignee: Syqe Medical Ltd., Tel-Aviv (IL)

( * ) Notice: Subject to any disclaimer, the term of this patent is extended or adjusted under 35 U.S.C. 154(b) by 1464 days.

(21) Appl. No.: 16/605,233

(22) PCT Filed: Apr. 18, 2018

(86) PCT No.: PCT/IL2018/050442
§ 371 (c)(1),
(2) Date: Oct. 15, 2019

(87) PCT Pub. No.: WO2018/193456
PCT Pub. Date: Oct. 25, 2018

(65) Prior Publication Data
US 2020/0121868 A1    Apr. 23, 2020

Related U.S. Application Data

(60) Provisional application No. 62/487,583, filed on Apr. 20, 2017.

(51) Int. Cl.
*A61M 15/00*    (2006.01)

(52) U.S. Cl.
CPC ...... *A61M 15/0021* (2014.02); *A61M 15/002* (2014.02); *A61M 15/009* (2013.01);
(Continued)

(58) Field of Classification Search
CPC .......... A24F 40/20; A24F 40/53; A24F 40/85; A61M 15/002; A61M 15/0021;
(Continued)

(56) References Cited

U.S. PATENT DOCUMENTS 2,513,145 A    6/1950   Chapple
5,337,740 A    8/1994   Armstrong et al.
(Continued)

FOREIGN PATENT DOCUMENTS

GB     2407042       4/2005
KR     10-1319228    10/2013
(Continued)

OTHER PUBLICATIONS

Communication Pursuant to Article 94(3) EPC Dated Jun. 23, 2022 From the European Patent Office Re. Application No. 18725666.4. (5 Pages).
(Continued)

*Primary Examiner* — Bradley H Philips

(57) ABSTRACT

According to some embodiments there is provided a replaceable flow tract for use with an inhaler device which delivers at least one substance to a user, the inhaler device comprising a housing shaped to receive the flow tract and to further receive a construct comprising source material from which the at least one substance is released; the replaceable flow tract comprising: a conduit comprising: a first opening; a second opening configured for being in fluid communication with a mouthpiece; and a third opening having an elastic sealing member extending therefrom, the elastic sealing member shaped and sized for pressing against the construct when the construct is within the housing.

15 Claims, 17 Drawing Sheets

(52) U.S. Cl.
CPC .............. *A61M 2202/064* (2013.01); *A61M 2205/0272* (2013.01); *A61M 2205/121* (2013.01); *A61M 2205/3653* (2013.01)

(58) Field of Classification Search
CPC .. A61M 15/23; A61M 15/0028; A61M 15/06; A61M 11/041; A61M 11/042; A61M 2205/11; A61M 2205/12; A61M 2205/121; A61M 2205/127; A61M 2205/273
See application file for complete search history.

(56) References Cited

U.S. PATENT DOCUMENTS

| | | | |
|---|---|---|---|
| 6,039,042 | A | 3/2000 | Sladek |
| 6,401,712 | B1 | 6/2002 | von Schuckmann |
| 8,490,627 | B2 | 7/2013 | Levin et al. |
| 9,943,114 | B2 | 4/2018 | Batista |
| 2003/0209245 | A1* | 11/2003 | Poole ................ A61M 15/0025 128/203.15 |
| 2008/0092912 | A1* | 4/2008 | Robinson ................ H05B 3/42 131/200 |
| 2009/0293892 | A1 | 12/2009 | Williams et al. |
| 2012/0255546 | A1* | 10/2012 | Goetz ................ A61M 11/042 128/202.21 |
| 2012/0304990 | A1 | 12/2012 | Todd |
| 2012/0325227 | A1 | 12/2012 | Robinson et al. |
| 2016/0089507 | A1 | 3/2016 | Dyche et al. |
| 2016/0345630 | A1 | 12/2016 | Mironov et al. |
| 2017/0099877 | A1* | 4/2017 | Worm ................ A24F 40/70 |
| 2018/0169357 | A1* | 6/2018 | Reevell ................ A61M 15/06 |
| 2019/0208820 | A1* | 7/2019 | Reevell ................ A24F 7/02 |

FOREIGN PATENT DOCUMENTS

| | | | |
|---|---|---|---|
| WO | WO 2016/001925 | 1/2016 | |
| WO | WO 2016/005533 | 1/2016 | |
| WO | WO-2016001925 A1 * | 1/2016 | .......... A24F 47/008 |
| WO | WO 2018/193456 | 10/2018 | |

OTHER PUBLICATIONS

Examination Report Dated May 16, 2023 From the Australian Government, IP Australia Re. Application No. 2018254265. (4 Pages).

Requisition by the Examiner Dated Nov. 27, 2023 From the Innovation, Science and Economic Development Canada, Canadian Intellectual Property Office Re. Application No. 3,059,679. (5 Pages).

International Preliminary Report on Patentability Dated Oct. 31, 2019 From the International Bureau of WIPO Re. Application No. PCT/IL2018/050442. (12 Pages).

International Search Report and the Written Opinion Dated Sep. 3, 2018 From the International Searching Authority Re. Application No. PCT/IL2018/050442. (23 Pages).

Invitation to Pay Additional Fees, Communication Relating to the Results of the Partial International Search and the Provisional Opinion Dated Jul. 9, 2018 From the International Searching Authority Re. Application No. PCT/IL2018/050442. (15 Pages).

Storz et al. "The Hot Air Generator Plenty", Storz & Bickel GmbH & Co. KG, User Manual, p. 3-33, Sep. 2016.

Storz et al. "The Mighty Vaporizer", Storz & Bickel GmbH & Co. KG, User Manual, p. 3-31, Sep. 2016.

Supplementary European Search Report and the European Search Opinion Dated Jun. 11, 2024 From the European Patent Office Re. Application No. 24163378.3. (10 Pages).

* cited by examiner

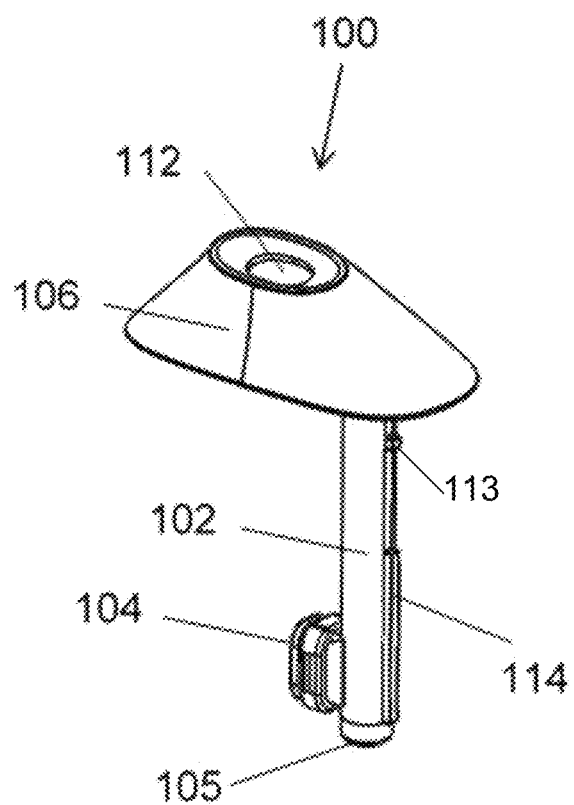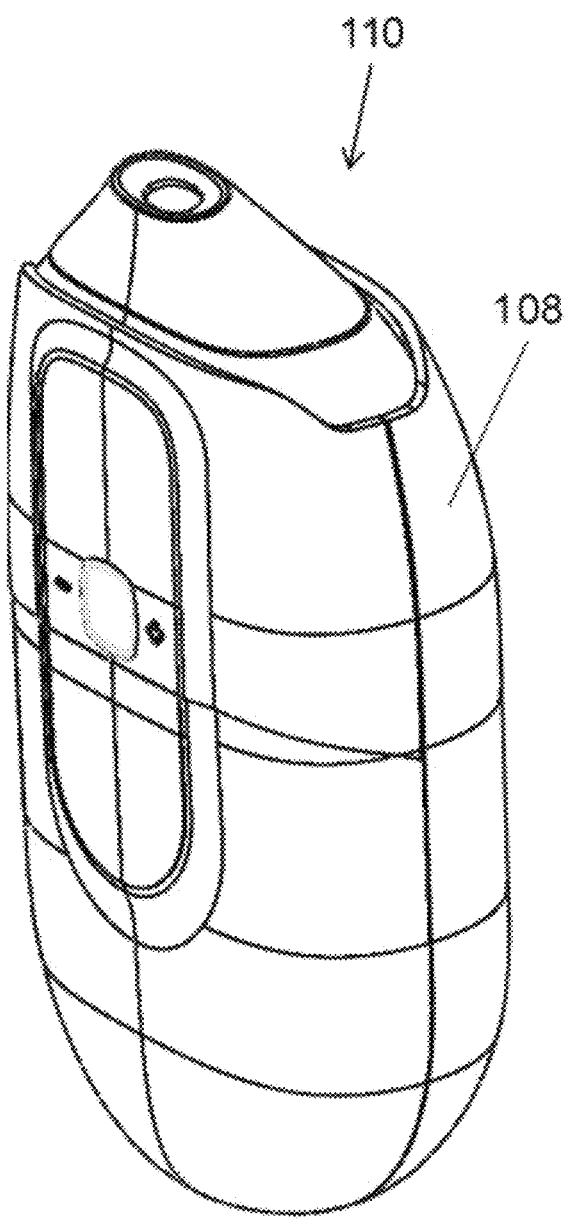
Fig. 1A
Fig. 1B

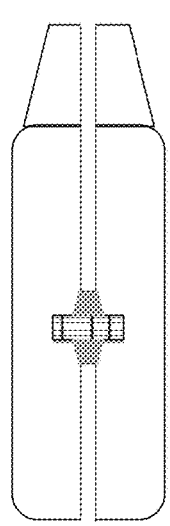
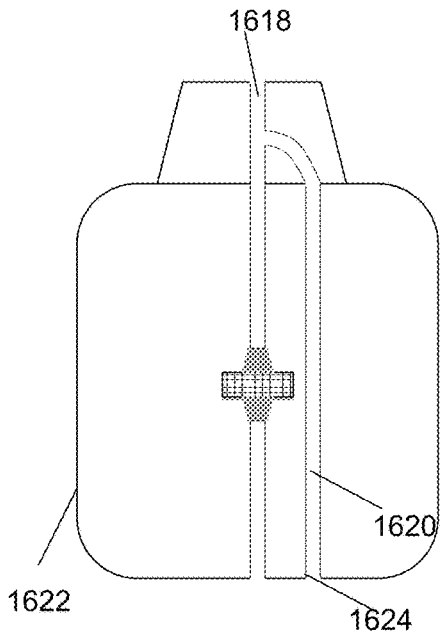
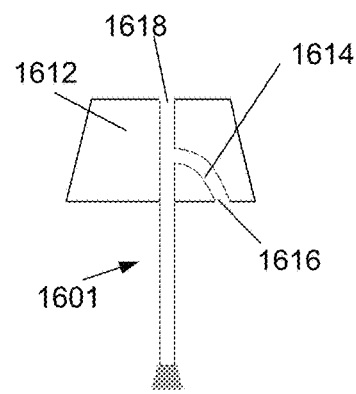
Fig. 16A
Fig. 16B
Fig. 16C
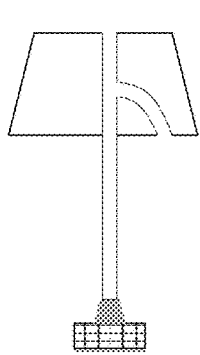
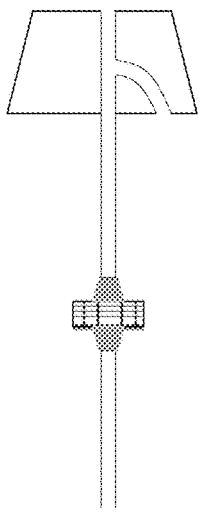
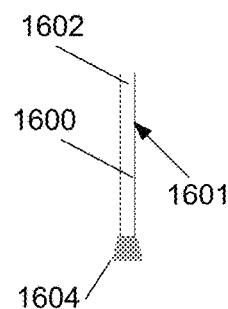
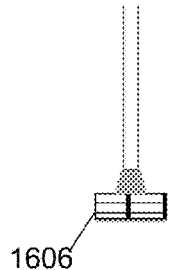
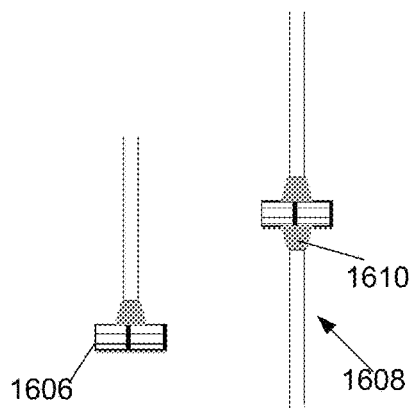
Fig. 16D
Fig. 16E
Fig. 16F
Fig. 16G
Fig. 16H

REPLACEABLE FLOW TRACT FOR AN INHALER

RELATED APPLICATIONS

This application is a National Phase of PCT Patent Application No. PCT/IL2018/050442 having International filing date of Apr. 18, 2018, which claims the benefit of priority of U.S. Provisional Patent Application No. 62/487,583 filed on Apr. 20, 2017. The contents of the above applications are all incorporated herein by reference.

FIELD AND BACKGROUND OF THE INVENTION

The present invention, in some embodiments thereof, relates to a replaceable flow tract for use with a device which delivers at least one substance to a user via inhalation.

U.S. Pat. No. 6,039,042 to Sladek discloses: "A medication inhalation apparatus for use with an MDI inhaler includes an elongated housing for receiving a plume of medication particles ejected by the MDI inhaler, a mouthpiece, and an inhalation valve disposed between the mouthpiece and the housing. An exhalation valve in the mouthpiece allows exhalation through the mouthpiece, presenting very little resistance to the exhalation effort of the patient. An adapter receives and stabilizes a mouthpiece of the MDI inhaler. The inhalation valve includes an inhalation membrane hanging adjacent to a valve seat. Exhalation into the mouthpiece presses the inhalation membrane against the valve seat, forcing exhaled gas through the exhalation valve. Inhalation causes the inhalation membrane to swing away from the valve seat and mostly out of a path of the medication plume. Impaction of medication particles against the inhalation membrane is avoided, and very little resistance is presented to the inhalation effort of the patient." (Abstract)

SUMMARY OF THE INVENTION

According to an aspect of some embodiments of the invention, there is provided a replaceable flow tract for use with a hand-held inhaler device which delivers at least one substance to a user, the inhaler device comprising a housing shaped to receive the flow tract and to further receive a construct comprising source material from which the at least one substance is released; the replaceable flow tract comprising: a conduit comprising: a first opening; a second opening configured for being in fluid communication with a mouthpiece; and a third opening having an elastic sealing member extending therefrom, the elastic sealing member shaped and sized for pressing against the construct when the construct is within the housing.

In some embodiments, when in use airflow is allowed to enter the conduit through the first opening and airflow imbued with the at least one substance is allowed to exit the conduit through the second opening.

In some embodiments, the third opening is configured along a wall of the conduit.

In some embodiments, the elastic sealing member is shaped to seal a coupling between a surface of the construct through which airflow passes and the conduit.

In some embodiments, the surface of the construct is essentially flat.

In some embodiments, the conduit comprises a smooth internal surface or lining.

In some embodiments, the internal surface is smooth at least to technical polish grade.

In some embodiments, the internal surface or lining is composed of one or more materials that are not adhesive to the at least one active substance.

In some embodiments, the flow tract is at least partially structured from oleophobic materials.

In some embodiments, the sealing member defines an aperture having an axis substantially perpendicular to a long axis of the conduit.

In some embodiments, the sealing member defines an aperture having an axis which is collinear with a long axis of the conduit.

In some embodiments, the sealing member comprises a base portion extending from the third opening of the conduit, and a widening portion extending from the base portion, the widening portion ending with a pliable lip sized to engage the construct.

In some embodiments, the flow tract is formed as a single integral unit.

In some embodiments, the flow tract comprises at least one element shaped and sized for at least one of guiding insertion of the flow tract and for locking the flow tract to the inhaler device.

In some embodiments, the at least one element comprises a protrusion extending from a wall of the conduit.

In some embodiments, the element is shaped and sized for both guiding insertion of the flow tract and for locking the flow tract to the inhaler device.

In some embodiments, the element sets a rotational position of the flow tract when the flow tract is received within the inhaler device.

In some embodiments, the element abuts against an internal wall within the inhaler device housing when the flow tract is received within the inhaler device housing to prevent unintentional pull-out of the flow tract from the housing.

In some embodiments, the element is an elongate protrusion extending along a longitudinal segment of the conduit.

In some embodiments, the elongate protrusion is rectangular.

In some embodiments, the flow tract comprises a mouthpiece defining an inclined surface tapering towards an opening.

In some embodiments, the conduit extends to the mouthpiece such that flow exiting the second opening exits the mouthpiece at the opening.

In some embodiments, the mouthpiece is coupled to the conduit by a threaded connection.

In some embodiments, the conduit defines a curvature within the mouthpiece such that it enters a bottom surface of the mouthpiece from a point which is not aligned with the opening of the mouthpiece and extends to a center of the opening of the mouthpiece.

In some embodiments, the curvature does not comprise a sharp bend.

In some embodiments, the conduit is a tube.

In some embodiments, a length of the conduit between the first and second openings is between 2-15 cm, and a diameter of the conduit is between 4-6 mm.

In some embodiments, the flow tract comprises one or more magnets for locking to the inhaler device by magnetic attraction. In some embodiments, the flow tract comprises one or more mechanical locking components for locking to the inhaler device by mechanical forces.

According to an aspect of some embodiments of the invention, there is provided an inhaler kit for delivery of at least one substance released from source material, the inhaler kit comprising: an inhaler housing comprising: a replaceable flow tract configured for extending between an output of the inhaler to a user and a location in which at least one substance is released from the source material; and a second, optionally permanent, flow tract positioned to direct ambient airflow to the location; the replaceable flow tract and second flow tract being configured for being aligned with respect to each other so as to come into sealed communication with each other, the sealed communication formed at the location.

In some embodiments, each of the replaceable flow tract and the second flow tract comprises a conduit including a sealing member, and when in use the second and replaceable flow tracts are aligned with respect to each other such that apertures of the sealing members face each other.

In some embodiments, the kit comprises at least one replaceable flow tract provided separately from the inhaler housing.

In some embodiments, the kit comprises two or more replaceable flow tracts.

In some embodiments, when in position within the housing the replaceable flow tract extends from the location of substance release to the output.

In some embodiments, at least one of the replaceable flow tract and the second flow tract is configured to be moved with respect to the other flow tract or with respect to the location.

In some embodiments, the inhaler housing comprises a motor configured for actuating movement of at least a portion of the second flow tract that includes the sealing member relative to the location of substance release.

In some embodiments, the portion of the second flow tract is configured to be moved between a first position in which the sealing member contacts a source material construct when the construct is placed at the location, and a second position in which the sealing member is distanced from the location.

In some embodiments, the kit comprises at least one cartridge containing at least one source material construct sized to be received within the inhaler housing at the substance release location.

In some embodiments, the at least one source material construct is sized and shaped so that when received at the location, the sealed communication is formed.

In some embodiments, an aperture defined by each of the sealing members is shaped according to an opening in the source material construct which exposes source material contained within the construct to the passage of air through.

In some embodiments, an aperture defined by each of the sealing members is rounded, oval, circular, or comprising a polygonal profile having rounded corners.

In some embodiments, the housing comprises circuitry for activating a heating element associated with the source material construct when the construct is received at the location. In some embodiments, the inhaler kit comprises at least one sensor positioned within the inhaler housing for sensing an indication of airflow rate at the location.

In some embodiments, the inhaler housing comprises a controller configured to receive an indication from the at least one sensor.

In some embodiments, the inhaler kit comprises one or more valves positioned to reduce or prevent backflow through the location.

In some embodiments, the sealed communication essentially prevents entry of air into the replaceable tract at the location that did not pass through the second flow tract.

In some embodiments, the sealed communication essentially prevents air that passed from the second flow tract into the location through the location from exiting in any direction other than into the replaceable flow tract.

In some embodiments, the replaceable flow tract defines an isolated pathway which prevents inhaler components external to the pathway from being exposed to residues of substance release.

According to an aspect of some embodiments of the invention, there is provided a sealing member for an inhaler device, the sealing member comprising: a base portion shaped to fittingly engage a conduit; and a widening portion extending from the base portion, the widening portion ending with a pliable rim that elastically deforms when pressed against a surface to seal a pathway between the surface and the conduit.

In some embodiments, one or more materials forming the sealing member are rigid enough to prevent collapsing of the sealing member when axial forces are applied to the sealing member.

In some embodiments, the one or more materials forming the sealing member are elastic enough so that when pressed against the surface a contact surface area between the sealing member and the surface increases.

In some embodiments, the contact surface area of the pliable rim with the surface increases by at least 30% when the sealing member is pressed against the surface.

In some embodiments, the surface increases by at least 30% when the sealing member is pressed against the surface by an axial force of between 20-50N or between 30-40 N.

In some embodiments, the sealing member is configured to withstand axial forces of between 20-50N or between 30-40N.

In some embodiments, the axial forces comprise force applied in a direction parallel to a thickness of the sealing member.

In some embodiments, one or more materials forming the sealing member are heat resistant at temperatures of up to 250 degrees Celsius.

In some embodiments, one or more materials forming the sealing member are heat resistant at temperatures of up to 300 degrees Celsius.

In some embodiments, the pliable rim is rectangular.

In some embodiments, the widening defines an undercut.

According to an aspect of some embodiments of the invention, there is provided a method of using an inhaler device comprising a replaceable flow tract, comprising: inserting a replaceable flow tract into a housing of the inhaler device; locking the flow tract with respect to the housing; inhaling at least one active substance from the inhaler device, the active substance delivered only via the replaceable flow tract; and retracting the flow tract from the housing.

In some embodiments, a timing of retracting is selected according to one or more of: a number of inhalation sessions performed, a predefined period of time for using the flow tract, and a predefined amount of active substance delivered through the flow tract.

In some embodiments, a timing of retracting is selected according to a regimen prescribed to a user.

In some embodiments, inserting comprises advancing the flow tract into a designated recess in the housing, and locking comprises rotating the flow tract within the housing to a locked position.

In some embodiments, locking is guided by magnetic attraction. In some embodiments, locking is guided by a mechanical lock-in mechanism.

According to an aspect of some embodiments of the invention, there is provided a hand-held inhaler device for delivery of at least one substance to a user, the inhaler device comprising: a housing defining a location in which the at least one substance is released from source material; one or more valves positioned to prevent backflow of air through the location; and a controller configured to control a position of the one or more valves.

In some embodiments, at least one of the valves is positioned between the location and an opening of the housing through which ambient air enters the location.

In some embodiments, the controller is configured to prevent backflow of air through the location at least by controlling a position of a valve positioned between the location and an opening of the housing through which ambient air enters the location.

In some embodiments, the controller is configured to control, by changing a position of the one or move valves, relative airflow between an airflow path passing through the location and an alternative airflow path passing through the housing and not passing through the location.

In some embodiments, the inhaler device comprises one or more sensors for sensing flow through the location, and wherein the controller is configured to change a position of the one or more valves according to an indication received from the one or more pressure sensors.

According to an aspect of some embodiments of the invention, there is provided a replaceable flow tract for use with an inhaler device, the inhaler device comprising a housing shaped to receive the flow tract within the housing, the replaceable flow tract comprising: a first opening; a second opening configured for being in fluid communication with a mouthpiece; and a third opening having an elastic sealing member extending therefrom; wherein the flow tract comprises at least one element shaped and sized for at least one of guiding insertion of the flow tract and for locking the flow tract to the inhaler device.

According to an aspect of some embodiments of the invention, there is provided a replaceable flow tract for use with a hand-held inhaler device which delivers at least one substance to a user, the inhaler device comprising a housing shaped to receive the flow tract, the housing defining at least one opening through which ambient air enters; the replaceable flow tract comprising: a conduit comprising: a first opening through which airflow is allowed to enter the conduit; a second opening through which airflow imbued with the at least one active substance is allowed to exit the conduit, the second opening configured for being in fluid communication with a mouthpiece; a third opening configured along a wall of the conduit, the third opening having: an elastic sealing member extending therefrom; and at least one element extending from conduit, the element shaped and sized for at least one of guiding insertion of the flow tract and for locking the flow tract to the inhaler device.

According to an aspect of some embodiments of the invention, there is provided a replaceable flow tract for use with a hand-held inhaler device which delivers at least one substance to a user, the inhaler device comprising a housing shaped to receive the flow tract and to further receive a construct comprising source material from which the at least one substance is released; The replaceable flow tract comprising: a conduit comprising: an opening configured for being in fluid communication with a mouthpiece; and one or more of: a second opening having an elastic sealing member extending therefrom, the elastic sealing member shaped and sized for pressing against the construct when the construct is within the housing; and at least one element shaped and sized for at least one of guiding insertion of the flow tract and for locking the flow tract to the inhaler device.

According to an aspect of some embodiments of the invention, there is provided an inhaler for delivery of at least one substance released from source material, the inhaler comprising: an inhaler housing configured to hold: a replaceable flow tract extending between an output of the inhaler to a user and a location in which at least one substance is released from the source material; and a second flow tract positioned to direct ambient airflow to the location; wherein the replaceable flow tract and second flow tract are configured for being aligned with respect to each other so as to come into sealed communication with each other, the sealed communication formed at the location.

In some embodiments, the second flow tract is permanent.

In some embodiments, each of the replaceable flow tract and the second flow tract comprises a conduit including a sealing member, and wherein in use the second and replaceable flow tracts are aligned with respect to each other such that apertures of the sealing members face each other.

In some embodiments, at least one of the replaceable flow tract and the second flow tract is configured to be moved with respect to the other flow tract or with respect to the location.

In some embodiments, the inhaler housing comprises a motor configured for actuating movement of at least a portion of the second flow tract that includes the sealing member relative to the location of substance release.

In some embodiments the portion of the second flow tract is configured to be moved between a first position in which the sealing member contacts a source material construct when the construct is placed at the location, and a second position in which the sealing member is distanced from the location.

In some embodiments, the inhaler is configured to receive at least one source material construct sized to be received within the inhaler housing at the substance release location. Optionally, the inhaler is configured to obtain the at least one source material construct from a cartridge containing a plurality of such source material constructs.

In some embodiments, the at least one source material construct is sized and shaped so that when received at the location, the sealed communication is formed.

In some embodiments, an aperture defined by each of the sealing members is shaped according to an opening in the source material construct which exposes source material contained within the construct to the passage of air through.

In some embodiments, an aperture defined by each of the sealing members is rounded, oval, circular, or comprising a polygonal profile having rounded corners.

In some embodiments, the housing comprises circuitry for activating a heating element associated with the source material construct when the construct is received at the location.

In some embodiments, the inhaler comprises at least one sensor positioned within the inhaler housing for sensing an indication of airflow rate at the location.

In some embodiments, the inhaler housing comprises a controller configured to receive an indication from the at least one sensor.

In some embodiments, the inhaler comprises one or more valves positioned to reduce or prevent backflow through the location.

In some embodiments, the sealed communication essentially prevents entry of air into the replaceable tract at the location that did not pass through the second flow tract.

In some embodiments, the sealed communication essentially prevents air that passed from the second flow tract into the location through the location from exiting in any direction other than into the replaceable flow tract.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-B illustrate an inhaler device and a replaceable flow tract for use in the inhaler device, according to some embodiments;

FIG. 2 is a flowchart describing a method of using a replaceable flow tract, according to some embodiments;

FIGS. 3A-D illustrate a process of inserting a replaceable flow tract into an inhaler device, according to some embodiments;

FIG. 4 schematically illustrates a replaceable flow tract positioned within an inhaler device, according to some embodiments;

FIG. 5 is a flowchart describing mechanical operation of an inhaler device, according to some embodiments;

FIG. 6 schematically illustrates a replaceable flow tract for use in an inhaler device, according to some embodiments;

FIGS. 7A-B schematically illustrate clamping of a source material construct between a replaceable flow tract and a permanent unit, according to some embodiments;

Figure 9A:
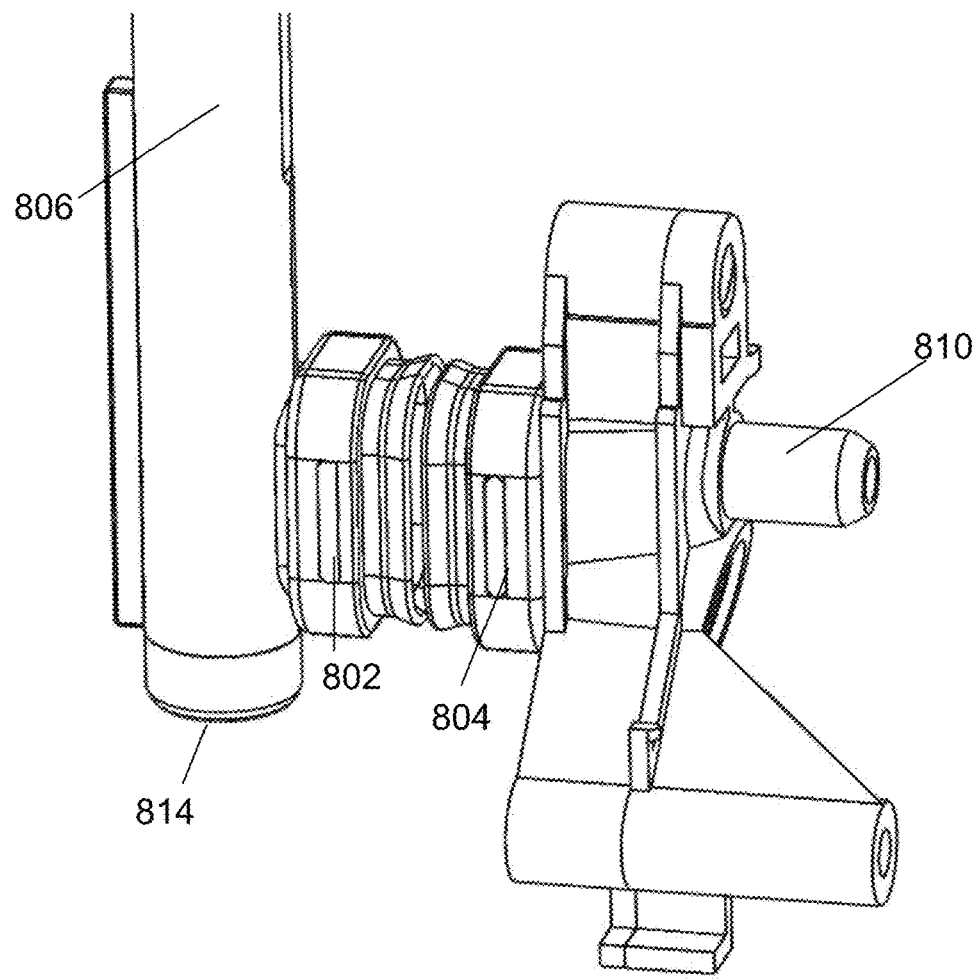
Figure 9B:
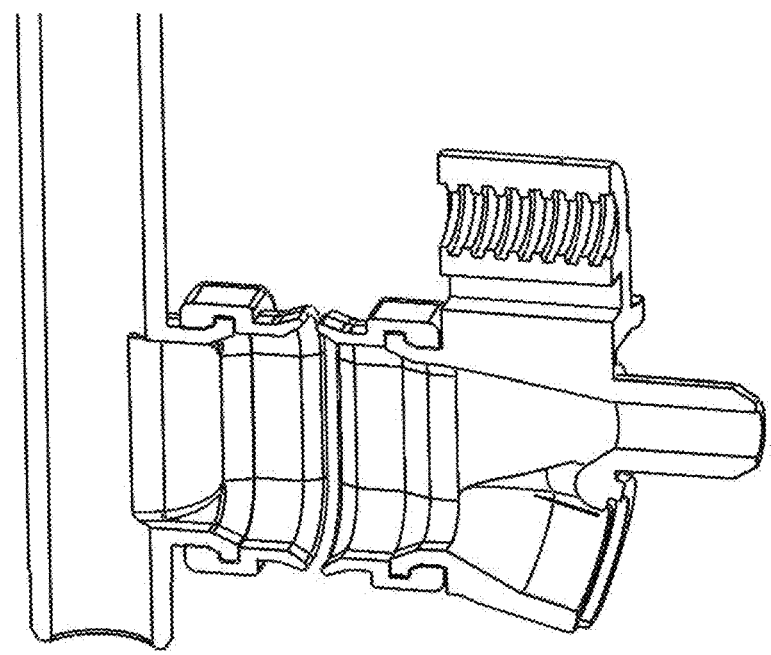
Figure 10A:
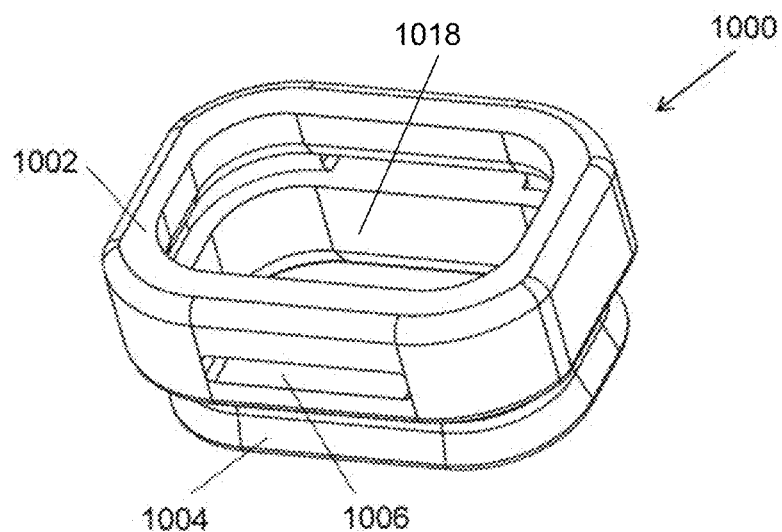
Figure 10B:
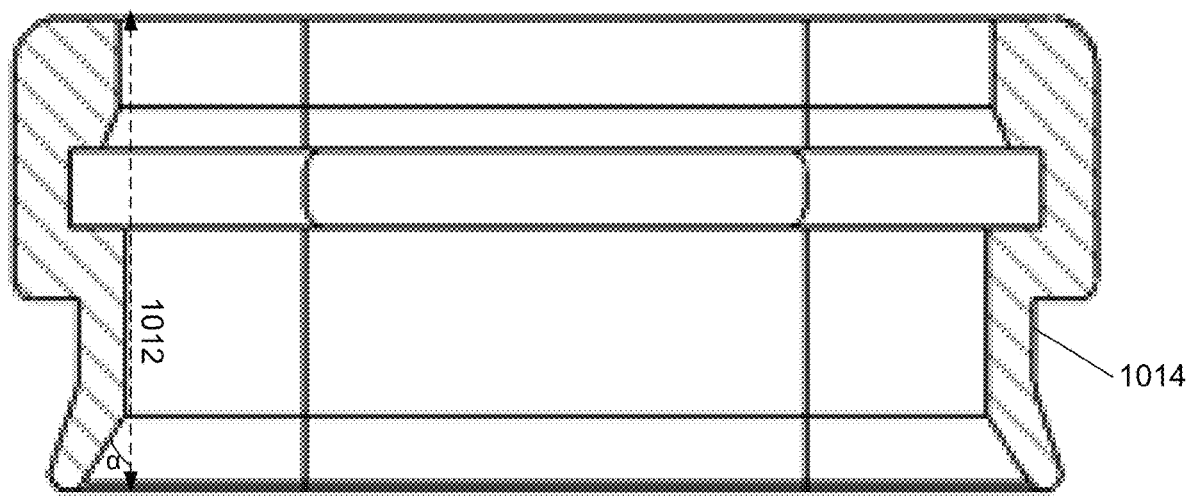
Figure 11A:
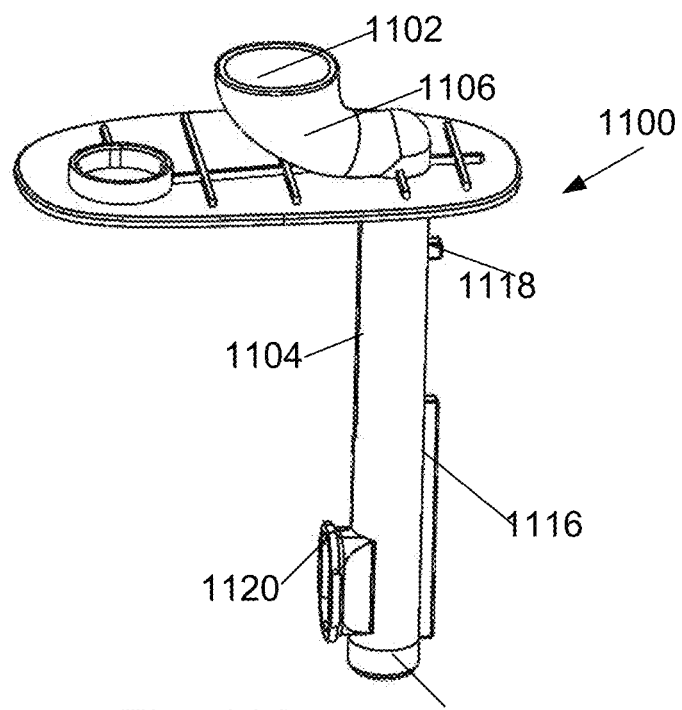
Figure 11B:
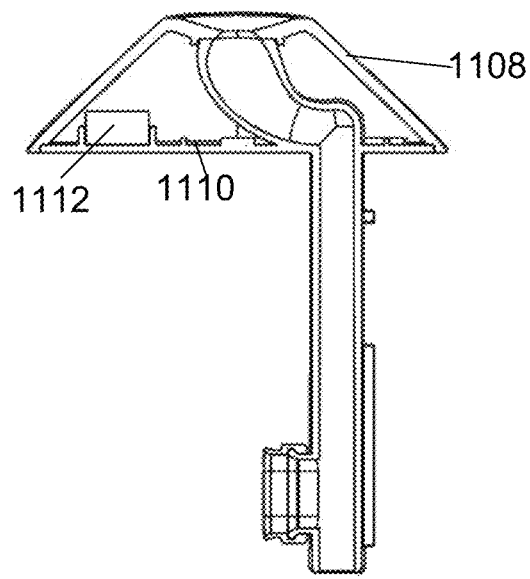
Figure 12:
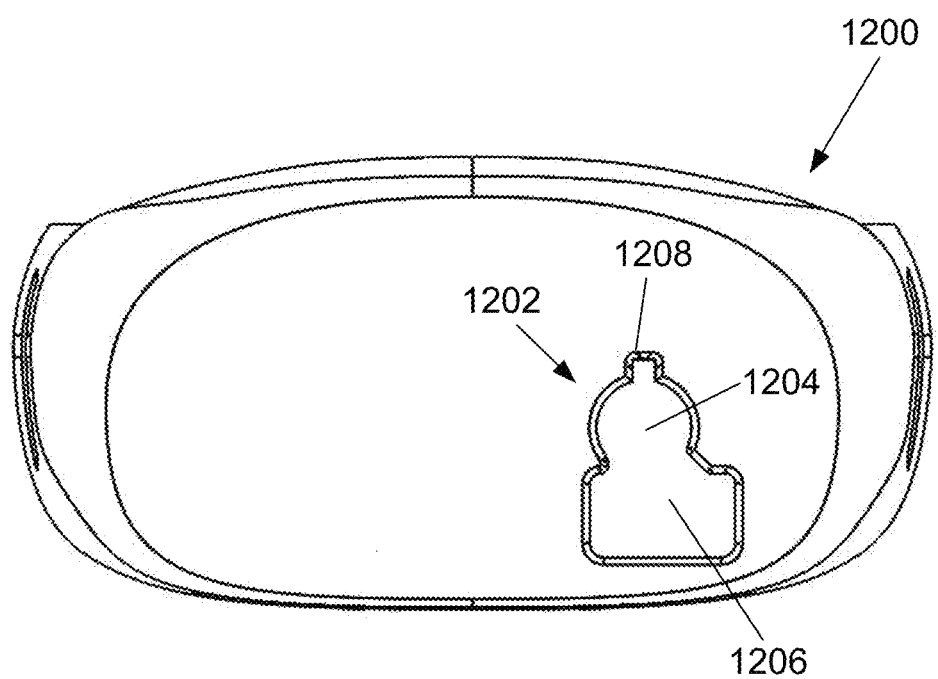
Figure 14:
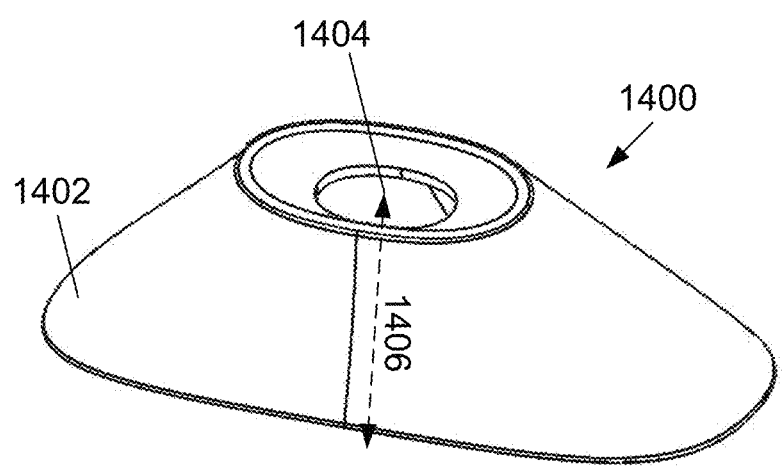
Figure 15A:
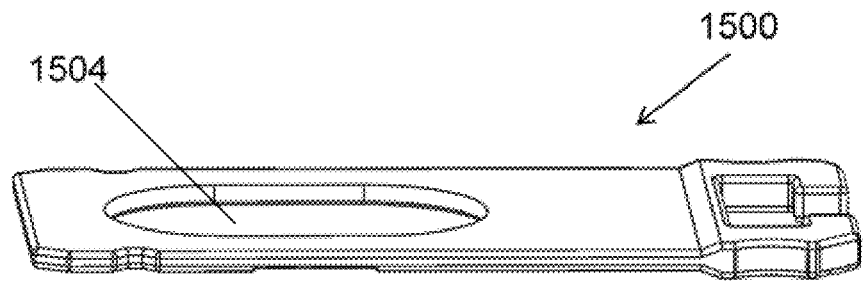
Figure 15B:
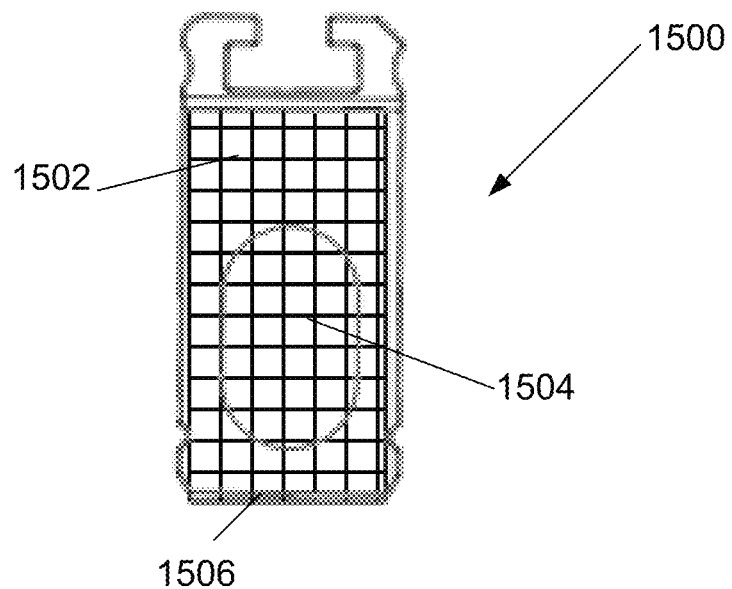

FIGS. 9A-B are a side view and a cross sectional view of the replaceable flow tract positioned near the permanent unit, according to some embodiments;

FIGS. 10A-B are an isometric view and a cross sectional view of a sealing member, according to some embodiments;

FIGS. 11A-B illustrate a replaceable flow tract (FIG. 11A) and a replaceable flow tract comprising and/or received within a mouthpiece (FIG. 11B), according to some embodiments;

FIG. 12 is a top view of an inhaler housing configured to receive a replaceable flow tract, according to some embodiments;

FIGS. 13A-F are examples of source material constructs and respective openings of matching sealing members, according to some embodiments;

FIG. 14 illustrates a replaceable mouthpiece, according to some embodiments;

FIGS. 15A-B show a source material construct, according to some embodiments; and FIGS. 16A-H are various schematic layouts of replaceable flow tracts (FIGS. 16C-H) for use with an inhaler device, and FIGS. 16A-B are schematic layouts of inhaler devices comprising replaceable flow tracts, according to some embodiments.

DESCRIPTION OF SPECIFIC EMBODIMENTS OF THE INVENTION

An aspect of some embodiments of the invention relates to a replaceable flow tract for use with an inhaler device which is configured to deliver at least one substance to a user via inhalation. In some embodiments, the at least one substance is vaporized, aerosolized, extracted and/or otherwise released from one or more source materials.

In some embodiments, the replaceable flow tract, when fitted within the inhaler device, sets an isolated pathway that extends from a position of the source material to an output to a user.

Optionally, permanent inhaler components remain unexposed (or essentially unexposed) to the active substance(s) released from the source material, for example to vapors of the active substance, as the vapors flow only through the sealed flow tract.

In some embodiments, the replaceable flow tract comprises a conduit, defining a first opening through which air is allowed to flow into the conduit; a second opening through which substance imbued air exits the conduit to be delivered to the user; and a third opening from which a sealing member extends. Optionally, the conduit is T shaped. Optionally, the conduit is Y-shaped. In some embodiments, a mouthpiece is mounted at the second opening.

In use, the flow tract is inserted into a housing of the inhaler device and maneuvered into a final locking position. Optionally, insertion and/or maneuvering and/or locking is guided by one or more structures (e.g. protrusions and/or cross sections and/or recesses) configured along the conduit, which correspond to respective shapes (e.g. recesses, cross sections or protrusions, respectively) in the inhaler housing. In some embodiments, the flow tract attaches to the housing by interference coupling.

In some embodiments, inserting and/or maneuvering of the flow tract is guided by magnetic attraction, for example a mouthpiece of the flow tract may be directed by magnets into a position in which the mouthpiece is aligned with a top surface of the inhaler housing. In some embodiments, inserting and/or maneuvering and/or fixing in position of the flow tract is guided by one or more mechanical components, for example a mouthpiece of the flow tract may comprise either a "female" mechanical part or a "male" mechanical part, once the mouthpiece arrives at the desired position, in which the mouthpiece is aligned with a top surface of the inhaler housing, the mechanical parts fit with a counterpart (either male or female) located on the top surface of the inhaler housing. Optionally, a magnet arrangement and/or other fasteners or connectors hold the flow tract in position. In some embodiments, one or more of the elements which guide the flow tract into position also lock the flow tract to the housing. Alternatively, the one or more elements which guide the flow tract into position are different than the one or more elements which lock the flow tract to the housing.

In some embodiments, at the final position, the sealing member of the flow tract faces a position of a source material construct. In some embodiments, an opposing permanent unit of the inhaler is located across from the sealing member, such that when a source material construct is in place, the construct is positioned in-between the sealing member of the flow tract and the opposing sealing member of the permanent unit. In some embodiments, the permanent unit is moveable between a first position in which its sealing member is pressed against the source material construct, which in turn presses the sealing member of the flow tract, forming a sealed path that extends through the source material of the construct and leads to the conduit of the flow tract, and a second position in which the two sealing members are spaced apart to as not to interfere with replacing of the source material construct therebetween.

In some embodiments, the sealing members remain stationary, and the source material construct is moved into a position in between the sealing members.

Optionally, the pliability of the sealing members is sufficient to enable "shoving" of the source material construct in-between the two members, while maintaining a sealed engagement. In some embodiments, one or both of the sealing members comprise a phase changing material. Optionally, when the sealing member is heated (for example as a result of heat transfer from the heated constructed), the phase changing material deforms (e.g. expands) to compress the construct in between the two sealing members, defining a sealed path.

In some embodiments, apertures of the sealing members are shaped to encompass and/or match an opening in the source material construct in which the source material is contained, allowing air to flow through from a direction of the permanent unit, into the sealing member of the permanent unit, through the source material, into the sealing member of the flow tract and into the conduit of the flow tract. A potential advantage of such arrangement may include that incoming airflow carries all of the substances released from the source material into the replaceable conduit, while not allowing the permanent unit to be exposed to the substances so released.

In some embodiments, the flow tract is replaced periodically, for example every day, every 2-5 days, every 1 week or longer, every 3 weeks or longer, every 1 month or longer, every 3 months or longer, or intermediate, longer or shorter time periods. Additionally or alternatively, the flow tract is replaced in accordance with an amount and/or type of active substance delivered. For example, for THC released from cannabis this may be every 25-250 mg, or every 35-150 mg or every 50-75 mg THC, or intermediate, larger or smaller amounts. Additionally or alternatively, the flow tract is replaced in accordance with the number of inhalation sessions performed. In some embodiments, a timing for replacing the flow tract is set according a prescribed regimen of the user, and/or according to user preference.

A potential advantage of an inhaler with a replaceable flow tract may include maintaining an efficiency of the inhaler device over time, as delivery of the active substance(s) may be affected by condensation of vapors and/or build-up of active substance residue and/or accumulation of byproducts of heating along the delivery path. By replacing the flow tract, such buildup may be maintained at a low level.

Another potential advantage of replacing the flow tract may include reducing a risk of contamination, as device portions interfacing with the user such as the mouthpiece are replaced. Contamination may, for example, be a result of contact with saliva and/or teeth and/or lips, bioburden accumulation and/or others. A replaceable flow tract may be especially advantageous when the source material comprises a botanical substance, for example when cannabis and/or tobacco are used.

In some embodiments, a kit is provided, comprising an inhaler device and one or more replaceable flow tracts for use with the inhaler. Optionally, the kit comprises one or more source material constructs, for example a cartridge comprising a plurality of source material constructs. Optionally, the inhaler comprises a plurality of source material constructs. Optionally, an inhaler is provided comprising one or more replaceable flow tracts. Optionally, replacement flow tracts are provided separately.

An aspect of some embodiments relates to sealing a flow path through which at least one substance is delivered. Some embodiments include a sealing member shaped to be pressed against a source material construct such that an aperture defined by walls of the sealing member is aligned with the source material construct which, in operation, is to release the substance.

Some embodiments include a sealing member shaped to be pressed against a source material construct such that an aperture defined by walls of the sealing member is aligned with an opening of the source material construct in which the source material is contained.

In some embodiments, the sealing member comprises a base portion configured to fittingly engage a conduit, and a widening extending from the base portion, the widening ending with a pliable lip. In some embodiments, the lip is elastic enough so that when pressed against the construct (or vice versa), a contact surface area between the sealing member and the construct is enlarged, preventing flow from escaping at the interface. In some embodiments, the sealing member may assist in dissipating heat away from the source material construct, from example from an electrically resistive mesh acting as a heating element of the source material.

As referred to herein, a "permanent" component may include a component of the inhaler device which is not intended for routine replacement, for example components that form an integral part of the inhaler device (e.g. a housing, a controller, a motor which actuates replacement of a source material construct, and/or others). Replacement of a "permanent" component is optionally performed by a qualified person, as part of resolving a malfunction of the device. A "replaceable" component as referred to herein may include a component intended for periodical replacement. Optionally, a replaceable component such as a replaceable flow tract is configured for manual and/or automatic attachment and/or detachment from permanent components, such as the inhaler housing. Optionally, such replacement is designed to be performed by an untrained user.

As referred to herein, a "conduit", for example a conduit of the replaceable flow tract, may include a pipe or tube which allows air to flow therethrough.

Optionally the tube is elongated and/or bifurcated or includes a plurality of connected tubes allowing flow from one to another. In some embodiments, the conduit comprises a tube that is rigid enough to maintain a path of airflow therethrough for example without support. Optionally, the tube is rigid enough to maintain its shape during insertion and/or removal of the replaceable flow tract to and from an inhaler device housing. For example being rigid may be taken to mean being rigid enough to transfer forces such as linear force (push or pull), torque and/or other forces, such as from one end of the conduit to the other. In some embodiments, flexion of the conduit is allowed to a certain extent, for example, one or more segments of the conduit may be slightly deformable and/or bendable. This may be advantageous for facilitating insertion and/or locking of the flow tract into the housing.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways. It is also to be understood that the invention is not necessarily limited in its application to the details set forth in the following description or exemplified by the Examples. The invention is capable of other embodiments or of being practiced or carried out in various ways.

FIGS. 1A-B are side views a replaceable flow tract (FIG. 1A) and an inhaler device in which the replaceable flow tract is received (FIG. 1B), according to some embodiments.

In the shown example, flow tract 100 comprises a main conduit 102 and a sealing member 104 extending from a side opening of the conduit. Optionally, the conduit comprises a first end defining an output to a user, for example comprising a mouthpiece 106, and a second end 105 which is open to allow flow of air through.

In some embodiments, flow tract 100 shaped and/or sized to be received within a housing 108 of inhaler device 110. In some embodiments, inhaler device 110 comprises and/or is configured to receive one or more source materials from which at least one substance is released to be delivered to a user via flow tract 100. In some embodiments, as will be further described hereinbelow, flow tract 100 is configured to be fitted at least in part within housing 108 such that sealing member 104 may engage a construct that contains the source material. In some embodiments, a portion of the flow tract, for example mouthpiece 106 or a part thereof (e.g. opening 112 through which the substance is delivered to the user) remains external to housing 108.

In some embodiments, flow tract 100 comprises a geometry configured to interact with the inner structure of the inhaler device, for example including one or more protrusions depicted for example as protrusion 113 extending outwardly from conduit 102. In some embodiments, positioning of the flow tract within the inhaler is guided by one or more protrusions depicted for example as protrusion 114, for example the protrusions may assist in rotationally orientating the flow tract within housing 108 to a locking position. In some embodiments, the one or more protrusions such as 113 and 114 extend from conduit 102 in a direction that faces away from sealing member 104. In such configuration, sealing member 104 does not mask the protrusions during advancement of the flow tract into the housing.

In some embodiments, when flow tract 100 is locked into position with respect to housing 108, vapors and/or aerosol of the released substance pass only via flow tract 100 from the source material construct all the way to the output to the user, thereby reducing or preventing exposure of permanent components of the inhaler to the active substance vapors. In some embodiments, when flow tract 100 is locked into position with respect to housing 108 sealing member 104 prevents the free entry of air that did not pass through the source material, thereby not affecting a flow, volume, temperature and/or pressure of air within the portion of flow tract 100 to which sealing member 104 is directly attached. A potential advantage of a flow tract that is entirely replaceable may include reducing or preventing damage to permanent components of the inhaler, for example damage due to vapor condensation, material residue or and/or other byproducts of active substance release. Another potential advantage of a flow tract that is entirely replaceable may include reducing malodor that may be due to condensate buildup.

In some embodiments, flow tract 100 including conduit 102, sealing member 104 and mouthpiece 106, is inserted into and/or removed from inhaler device 110 as a single integral unit. Alternatively, only some portions of the flow tract form a single integral unit, such as conduit 102 and sealing member 104, or conduit 102 and mouthpiece 106. Optionally, the flow tract is inserted into the housing as one piece.

In some embodiments, mouthpiece 106 is separable from flow tract 100.

Optionally, mouthpiece 106 is coupled to conduit 102 via a threaded coupling, a magnetic coupling, a snap fit coupling, and/or other mounting or coupling that enables detaching of the mouthpiece. In some embodiments, conduit 102 and sealing member 104 can be replaced while mouthpiece 106 is re-used by mounting it onto a conduit of a new flow tract replacing the removed one.

In some embodiments, conduit 102 and sealing member 104 and/or conduit 102 and mouthpiece 106 and/or all three components are manufactured as a single unit. In some embodiments, the flow tract or components thereof are produced using injection molding, double injection molding, casting, laser welding and/or other suitable techniques.

In some embodiments, a structure and/or materials of the flow tract are selected so as to reduce or prevent adhesion of the substance to the inner walls of the flow tract. In some embodiments, conduit 102 comprises a smooth internal surface or lining for reducing or preventing vapor condensation along the conduit. Optionally, the lining comprises material(s) that are not adhesive to the active substance(s) delivered. In some embodiments, flow tract 100 comprises materials that are selected according to the type of active substance released, for example selected to prevent absorbance of the active substance. In some embodiments, especially if the released active substances comprise cannabinoids (e.g. THC), oleophobic materials such as polypropylene, or silicone are used for constructing the flow tract or portions thereof such as an inner coating of conduit 102. In some embodiments, the flow tract is comprised of non-aromatic materials. Optionally, the flow tract or any part thereof is 3D printed.

In some embodiments, conduit 102 and/or mouthpiece 106 are formed of or comprise polypropylene. In some embodiments, sealing member 104 is formed of or comprises silicone. Other materials of the flow tract or components of it may include borosilicate glass, PEEK (polyetheretherketone), PTFE (Polytetrafluoroethylene, e.g., Teflon) and/or Viton.

Figure 2:
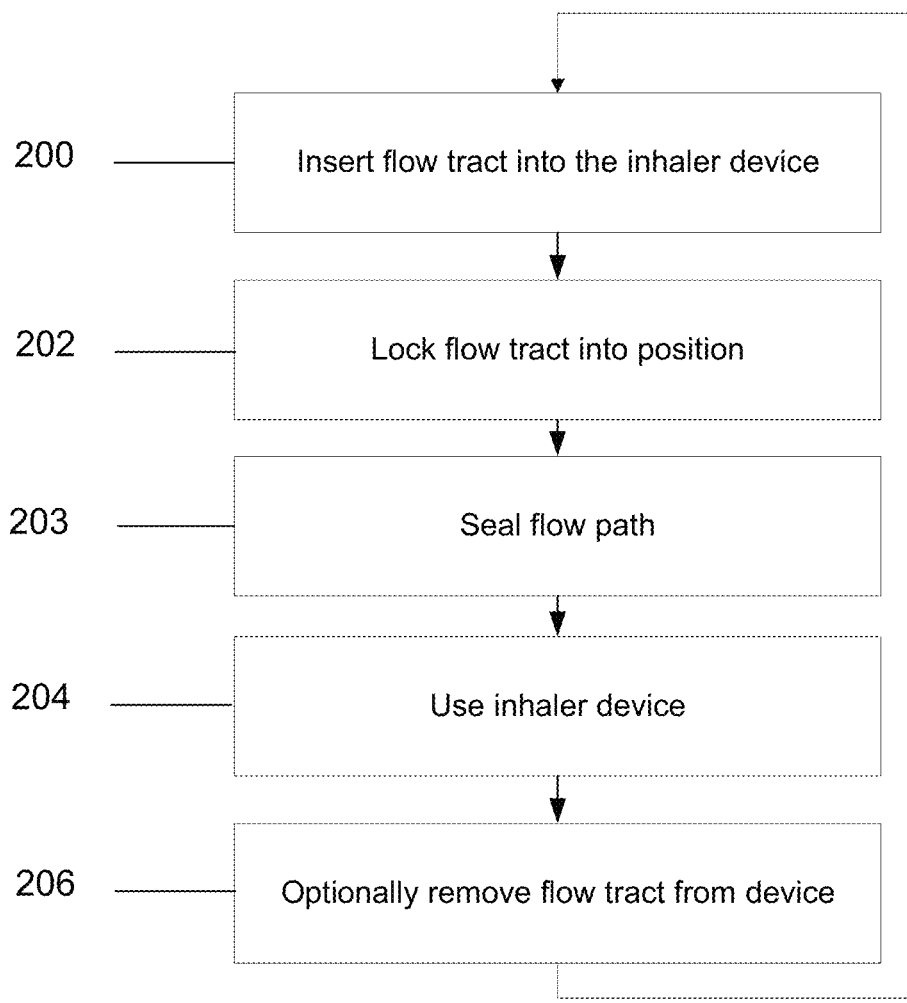

FIG. 2 is a flowchart of a method for using a replaceable flow tract, according to some embodiments.

At 200, a replaceable flow tract is inserted into an inhaler device. Optionally, the flow tract is pushed, twisted, and/or otherwise advanced into a housing of in the inhaler device. At 202, the flow tract is locked into position with respect to the housing and/or with respect to internal components of the inhaler device. Optionally, the flow tract snaps or into place.

In some embodiments, tactile feedback allows a user to sense that the flow tract is in place, for example by encountering resistance to further advancement of the flow tract into the housing and/or resistance to rotation and/or other sensible feedback.

Additionally or alternatively, an electrical circuit closes when the flow tract is in place. Additionally or alternatively, a light is blocked or activated within the inhaler, thereby triggering appropriate feedback to the user. Optionally, a visible indication such as a light indication (e.g. LED) and/or an audible indication is provided to the user to indicate that the flow tract is in place or, alternatively, not in place. Optionally, a notification is provided in case that the insertion is improper or incomplete and is removed or replaced with confirmation once the flow tract is in place. For example, this may be depicted on an LCD screen of the inhaler device or via an associated device (e.g. a cell phone application being in communication with the inhaler). In some embodiments, once the flow tract is in position, a flow path is defined between the source material construct and an output to the user, through which the active substance is delivered. At 203, a sealed flow path is formed. Optionally, the sealed flow path extends from the source material construct to an output to the user. In some embodiments, the source material construct is placed in between two opposing sealing members, and one or both of the sealing members are moved to clamp to source material construct in-between, sealing the flow path.

Additionally or alternatively, the construct is forced in between two sealing members that are held together or in very close proximity against each other. In embodiments where the construct is forced between sealing members, the distance between the sealing members is such that once the construct is in position, the airway between the sealing members is sealed. At 204, a user inhales from the inhaler device.

Optionally, a plurality of inhalation sessions are performed and/or a predefined period of time passes and/or a predefined amount of active substance is delivered to the user until the flow tract is removed and replaced, as shown at 206. In an example, the flow tract is replaced after 50 or less inhalation sessions, after 75 or less inhalation sessions, after 100 or less inhalation sessions, after 150 or less inhalation sessions, after 250 or less inhalation sessions, after 500 or less inhalation sessions or intermediate, larger or smaller number. In an example, the flow tract is replaced every day, every 2-5 days, every 1 week or longer, every 3 weeks or longer, every 1 month or longer, every 3 months or longer or intermediate, longer or shorter time periods. In an example in which THC is delivered to the user, the flow tract is replaced after 25-250 mg, or after 35-150 mg or after 50-75 mg THC, or any intermediate, larger or smaller amounts have been delivered.

In some embodiments, a timing for replacing the flow tract is set according to a regimen prescribed for the user. For example, for a user prescribed with frequent inhalation sessions and/or larger active substance amounts the flow tract may be replaced earlier or more often than it would for a user with less frequent inhalation sessions and/or a smaller amount of active substance delivered.

(In some embodiments, an "inhalation session" refers to an event over which a single dose of active substance is delivered to the user. Additionally or alternatively, an "inhalation session" refers to one activation of the inhaler device over which a dose is delivered to the user, comprising, for example, heating of sufficient source material to extract the dose and allowing flow of the vaporized active substance to the user.

Optionally, an "inhalation session" refers to one activation of the inhaler device during which the user inhales once) Optionally, the timing of replacement is imposed or proposed by a controller associated with the inhaler, such as a controller included in the inhaler and/or a software module in an associated device (for example a cell phone application) or system. Optionally, the user may replace the flow tract less frequently than proposed, but eventually replacement is imposed and the device is prevented from operating barring replacement of the flow tract.

In some embodiments, if the flow tract is not replaced and/or before expected replacement of the flow tract, the flow tract is cleaned and/or disinfected for removal of odor and/or active substance residues and/or other byproducts of use. Optionally, the flow tract is cleaned by insertion of a cleaning rod and/or using a cleaning fluid such as isopropanol, ethanol and/or detergent.

In some embodiments, the mouthpiece is washable and/or can be wiped clean.

In some embodiments, following removal of the flow tract, the flow tract is discarded. Alternatively, the flow tract is sterilized and/or otherwise cleaned to enable its reuse. In some embodiments, a user sends a used flow tract to a lab or other center for cleaning. Optionally, the flow tract is returned to the user.

In some embodiments, a flow tract shape and/or dimensions are selected to match a user's need or preference. In an example, a mouthpiece size may be selected in accordance with the size of the mouth of the user or based on user comfort. In another example, a width of the flow tract may be selected in accordance with the user's inhalation capacity.

FIGS. 3A-D illustrate a process of inserting a replaceable flow tract into an inhaler device, according to some embodiments.

Figure 3A:
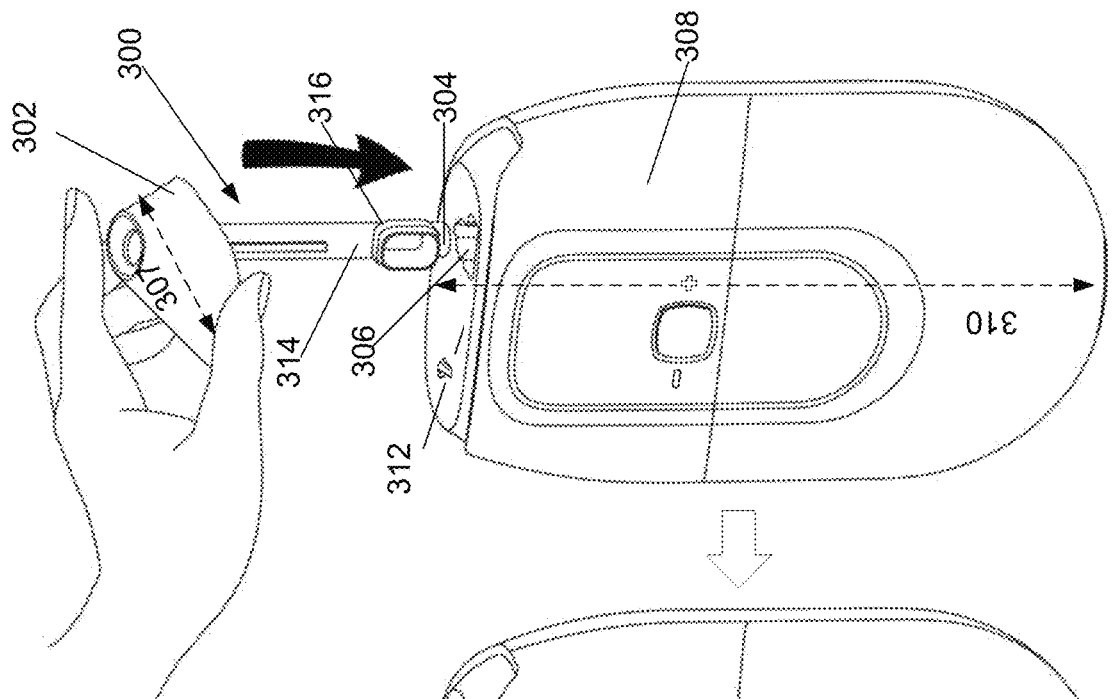

In some embodiments, as shown in FIG. 3A, a user grasps the replaceable flow tract 300 by the mouthpiece 302 and inserts an end 304 of the flow tract which is remoted from the mouthpiece into an opening 306 formed in top surface 312 of inhaler housing 308. As shown in this example, opening 306 is shaped and sized to fittingly accept the contour of the bottom portion of flow tract 300, thereby allowing the user to perform the insert only in the proper orientation. In the example shown herein, insertion of the flow tract is performed by holding mouthpiece 302 such that an axis 307 along the width of mouthpiece is at a 90 degree orientation with respect to a long axis 310 of inhaler housing 308.

Figure 3B:
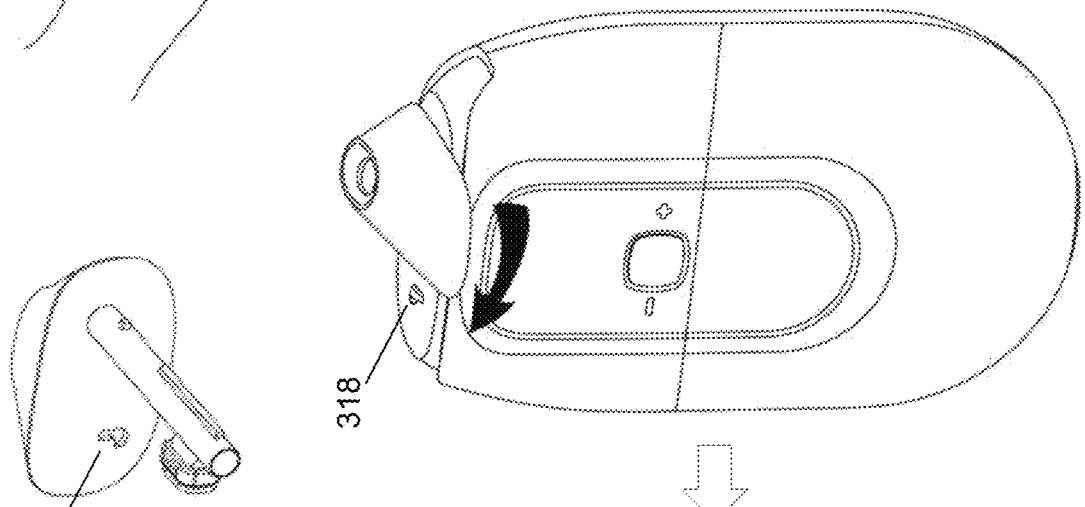
Figure 3D:
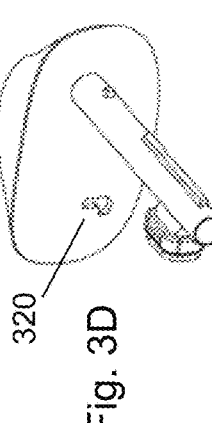
Figure 3C:
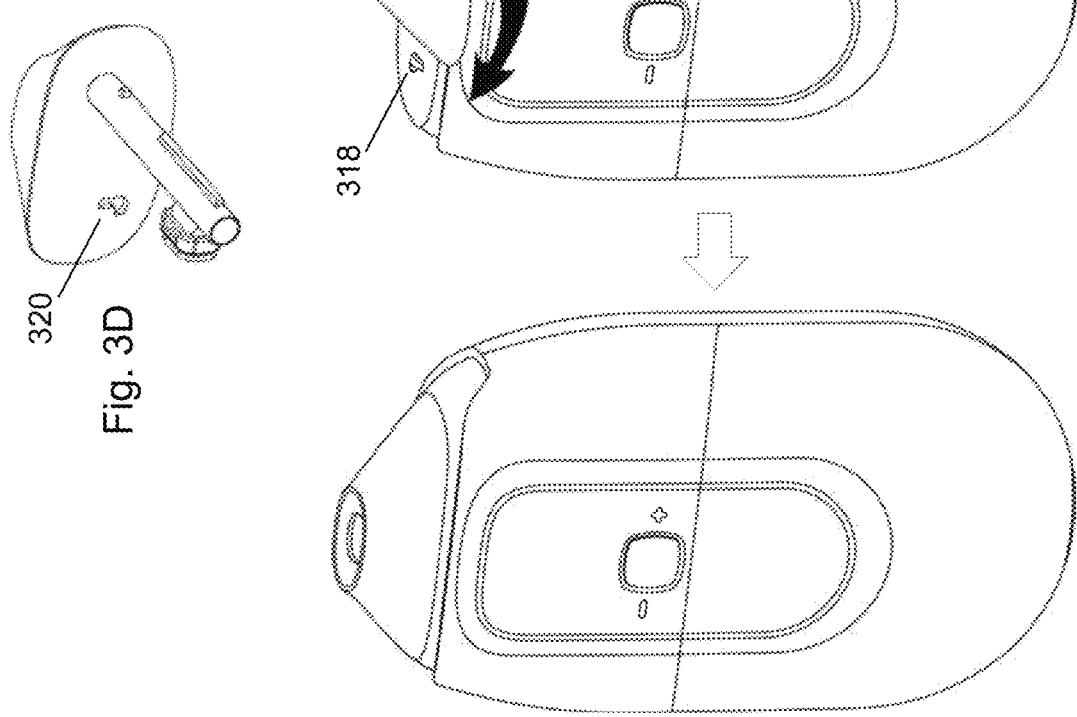

In some embodiments, flow tract 300 is advanced into housing 308 until a bottom surface of mouthpiece 302 encounters top surface 312 of the housing, as shown in FIG. 3B. At this point, mouthpiece is rotated by 90 degrees to be aligned with top surface 312, thereby rotating the rest of flow tract 300 (conduit 314 and sealing member 316) into a final locked position, as shown in FIGS. 3B and 3C. In some embodiments, the flow tract is advanced into the housing and the mouthpiece is rotated just before or upon contacting the top surface of the housing. In some embodiments, the flow tract is inserted by screwing motion.

In some embodiments, when flow tract 300 is locked in position, sealing member 316 is aligned with a designated position of the source material construct (not shown in this drawing) and/or with the position of an opening of a second tract within the inhaler (also not shown in this drawing).

In some embodiments, mouthpiece 302 is guided into position and/or maintained in position on top surface 312 of housing 308 by magnetic force, for example by a pair of magnets positioned within mouthpiece 302 (optionally adjacent the bottom surface of the mouthpiece) and within housing 308 (optionally on or adjacent top surface 312). Additionally, or alternatively, other connectors including for example pins, clips, snaps may be used for holding mouthpiece 302 in position. For example, other connectors may be a mechanical "female-male" connector as shown in FIGS. 3A-B, where protrusion (male) 318 is configured to interlock with configured orifice (female) 320 (shown in FIG. 3D). In some embodiments, the lock mechanism described, for example by parts 318 and 320, enables the prevention of unintentional disengagement of the mouthpiece 302, ensures the proper positioning of the mouthpiece 302 and avoids the over rotation of the mouthpiece 302, that may cause damage to the same.

Optionally, maintaining an alignment between the mouthpiece and the housing keeps the rest of the flow tract (the conduit and the sealing member) in the set position.

In some embodiments, if the flow tract is initially not inserted properly, further advancement and/or rotation of the flow tract are not enabled.

In some embodiments, for retraction and removal of the flow tract from the device, the actions are performed in a reversed order: first the mouthpiece is twisted by 90 degrees, thus optionally releasing the tract from its locked position and aligning it with the extraction path. Then the mouthpiece is grasped and pulled back to retract the flow tract completely from the housing.

In some embodiments, the flow tract is releasable via a quick release mechanism, for example using spring actuation or the like. Optionally, the inhaler housing (and/or the mouthpiece portion of the flow tract) comprises a quick-release button.

Figure 4:
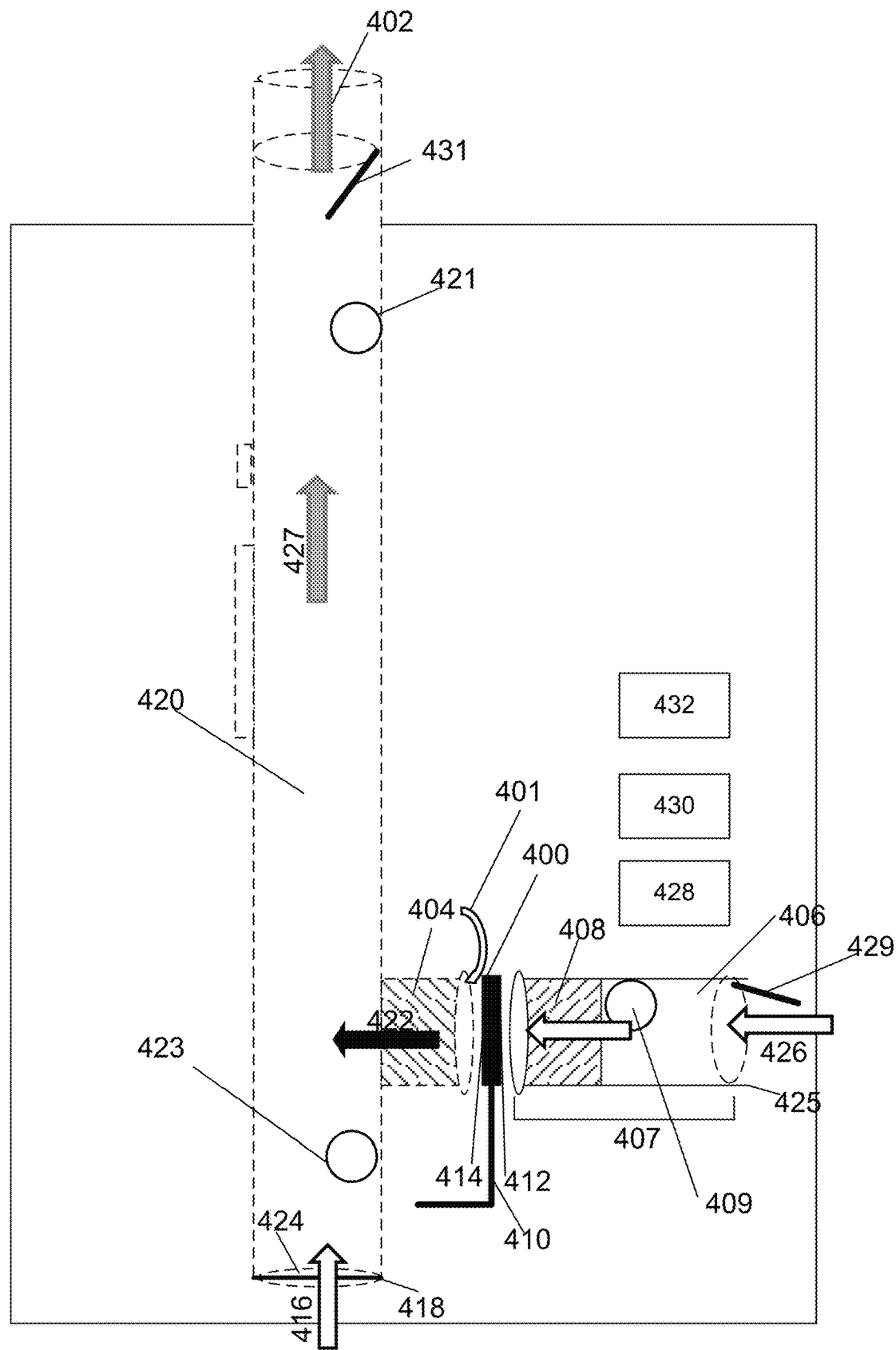

FIG. 4 schematically illustrates a replaceable flow tract positioned within an inhaler device, according to some embodiments.

In some embodiments, the replaceable flow tract (indicated by dashed lines) is received within the inhaler device (indicated by full lines), defining a flow path between source material construct 400 and an output 402 to a user.

In some embodiments, the flow tract is aligned such that an opening of a sealing member 404 is aligned with a position of source material construct 400. In some embodiments, a permanent unit 407, including a conduit 406 that ends with a second sealing member 408, is positioned opposite sealing member 404 such that an opening of second sealing member 408 is fully aligned with the opening of first sealing member 404 of the replaceable flow tract.

In some embodiments, source material construct 400 is held in between openings of the opposing sealing members, for example by a holder 410. In some embodiments, source material construct 400 comprises one or more source materials, for example plant materials such as cannabis, tobacco and/or one or more extracted, synthetic and/or purified substances (possible in association with a synthetic pallet comprising) and/or others. In some embodiments, the construct comprises a thin layer of ground plant material held by a frame which is at least partially air-permeable. In an example, the frame comprises two mesh portions extending across the layer of ground material. Further details of a source material construct in accordance with some embodiments are provided below.

In some embodiments, at least a part of the frame is electrically conductive so that when current is passed through, the source material is heated and the active substance(s) are vaporized. Optionally, the frame comes in contact with the contained source material so that heat is transferred by conduction. Additionally or alternatively, heating is provided by a heating element external to the source material construct, for example a heating element positioned within the inhaler housing adjacent the construct position. In an example, a heating element is coupled to holder 410.

In some embodiments, in use, permanent unit 407 is advanced in the direction of the flow tract, until second sealing member 408 is pressed against source material construct 400, for example against a surface 412 of the construct, thereby pressing an opposing surface 414 of the construct against first sealing member 404, forming a sealed flow path for the released vapors to flow through. In some embodiments, the permanent unit is pushed, rotated, slid, and/or otherwise advanced in the direction of the construct and the first sealing member. Optionally, the sealing formed between the two sealing members and across the construct ensures that at least 99%, 98%, 95% or intermediate, higher or lower percentage of the volume of flow entering first sealing member 404 is received directly from the permanent unit and the replaceable flow tract. In other words, in such embodiments, the sealing formed between the two sealing members and across the construct reduces or even prevents inflow of air from within the inhaler depicted for example schematically as arrow 401.

In some embodiments, in use, bypass airflow 416 enters the inhaler device via an opening 418 of conduit 420 of the replaceable flow tract. Optionally, the flow of air is regulated by a valve 424, by the size (e.g. diameter) of opening 418, and/or other means of regulating flow. In some embodiments, carrier airflow 426 enters via an opening 425 that leads to conduit 406 of the permanent unit 407. Optionally, air is drawn into one or both openings in response to inhalation by the user. Additionally or alternatively, a fan and/or other element suitable for causing air to enter the inhaler device is used, at least to cause or to augment carrier airflow 426.

In some embodiments, carrier airflow 426 that entered through conduit 406 then flows to and through second sealing member 408, passing through source material contained in construct 400. In some embodiments, heating of the source material is synchronized with the passing of air through (for example activated once airflow rate or pressure passes a predefined threshold), and air 422 imbued with the vaporized substance(s) leaves the construct and enters conduit 420 via first sealing member 404. In conduit 420, the substance-imbued air 422 and the bypass airflow 416 join to form combination airflow 427 and flow along conduit 420 until exiting the conduit from output 402.

In some embodiments, carrier airflow 426 through construct 400 is maintained at a constant, relatively rate, for example ranging between 0.5-2 liter/min or 0.7-1.5 liter/min or about 1 liter/min or intermediate, larger or smaller flow rates for at least a portion of a given inhalation. Optionally this portion of inhalation lasts at least 0.5 second or longer, 1 second or longer, 2 seconds or longer or about 3 seconds or any intermediate, longer or shorter portions of time.

Optionally, the constant flow through the construct is maintained by regulating the bypass flow 416. Flow mechanisms and/control thereof as described in PCT publication WO2016/001926 titled "FLOW REGULATING INHALER DEVICE" by Davidson are incorporated herein by reference.

In some embodiments, a rate of the bypass airflow 416 that joins the carrier airflow is between two folds to 7 folds the rate of the carrier airflow, producing a fast flowing active-substance imbued flow 422 along conduit 420. A potential advantage of relatively fast flowing, diluted active substance-imbued air through the replaceable flow tract may include reducing condensation of the active substance vapors along the inner walls of conduit 420. In some embodiments, one or more sensors such as 409, 423, 421, optionally pressure sensors, are used for sensing a parameter indicative of flow rate at one or more locations along the flow path. In some embodiments, sensor 409 is positioned to indicate a rate of airflow through the source material construct. Optionally, sensor 409 is positioned within conduit 406, optionally adjacent sealing member 408 such that it detects a rate of airflow entering the source material construct.

In some embodiments, controller 430 receives flow rate indications from the one or more sensors, and controls operation accordingly, for example controls the rate of bypass flow into the device according to indications received from sensor 409.

In some embodiments, during inhalation, a pressure drop occurs, as the user applies suction via the mouthpiece (not shown). In an event of exhalation, pressure levels may rise. In some embodiments, in such event the pressure rise is detected by the one or more pressure sensors, and in response the controller actuates one or more valves to prevent exhalation flow from reaching the source material construct, potentially undesirably carrying substances released from the construct into the permanent unit.

In some embodiments, controller 430 changes a position of one or more valves to produce an air path in which resistance to flow is reduced as compared to resistance of the flow path through the construct. Optionally, air entering in the direction of the construct encounters increased pressure (due for example to partial or complete closure of an exit valve) and flows through a less resistive path instead. In some embodiments, controller 430 actuates closure of a valve 429 positioned at opening 425 to reduce or even prevent backwards flow through conduit 406. Additionally or alternatively, the controller opens valve 418 to augment airflow through conduit 420.

Additionally or alternatively, a directional valve 431 positioned at conduit 420 and/or at the mouthpiece (not shown) serves to reduce or prevent exhalation flow from advancing through.

In some embodiments, a user is recommended to exhale after removing their mouth from the inhaler, so as to reduce or prevent exhalation into the device.

In some embodiments, indications received by the one or more sensors allow determining whether the sealing is tight enough. For example, an unexpected change in the flow rate values received from sensor 409 may indicate that air other than ambient air 426 might have passed through the construct, for example air entering at the interface between the sealing members (e.g. air entering along the periphery of the engaged lips of the sealing members depicted schematically as arrow 401). Optionally, in response to such indication, the controller actuates movement of one or both of the replaceable flow path and the permanent unit towards each other to obtain a tighter seal and/or prevents operation of the inhaler and alerts the user to a malfunction.

In some embodiments, the sealing should be tight enough to essentially prevent air other than air flowing through conduit 406 from entering the source material construct (e.g. airflow 426 accounts for at least 95% of the airflow entering sealing member 404). In some cases, if the sealing is not tight enough, entering air may affect the rate of flow through the construct, in which case an indication received from sensor 409 may not be accurate and potentially lead to erroneous control over the bypass flow entering the device.

In some embodiments, following use of the source material within construct 400, permanent unit 407 is retracted, leaving some space between the two sealing members. In some embodiments, a new construct (not shown herein) is moved into position between the two sealing members. The permanent unit 407 is then advanced back into a sealing position, pushing the new construct against the first sealing member, thereby defining again a sealed flow path through which active substances released from the new construct are delivered to the user.

In some embodiments, advancement and/or retraction of the permanent unit 407 is carried out by a motor 428, in response to a signal received from controller 430 of the inhaler device. In some embodiments, the permanent unit is advanced or retracted via threading and unthreading of a screw within a threaded passage.

In some embodiments, controller 430 controls one or more of: a position of valve 426, for example for regulating entering air flow; a position of one or more of valves 429, 418, 431, a timing and profile of heating of the source material construct (for example via dedicated circuitry); movement of the permanent unit; replacing of the source material construct (e.g. by a lever that moves a new construct into position); obtaining flow rate indications by the one or more sensors; and/or other device functions.

In some embodiments, the inhaler device is powered by a power source 432, for example comprising a rechargeable battery.

Further details of the source material construct 400 are provided by the following. In some embodiments, source material construct 400 comprises: a load of source material, optionally formed for rapid vaporization; mechanical support for the load of source material (for example, support by enclosure within a housing, which is optionally frame shaped); an attachment element for facilitating transport of the construct; and/or means for vaporizing the load of source material (for example, an electrically resistive heating element, optionally a mesh).

In some embodiments, the construct comprises a substantially flattened configuration, for example formed as an elongated strip. In some embodiments, the construct defines an aperture or chamber in which the source material is contained.

In some embodiments, the load of source material conforms to the shape of the construct, for example being thin enough so as not to protrude outwardly from the construct. Optionally, the source material load is in the form of a pallet. The pallet may have a thickness ranging between 0.2-1.5 mm, or a greater, lesser, or intermediate thickness.

In some embodiments, the construct frames the pallet of source material at least in part.

Enclosure within frame allows the source material load to be moved within the system without applying stresses directly to the source material and/or optionally renders the source material less sensitive to damage.

In some embodiments, the source material comprises plant material, for example tobacco and/or cannabis and/or other botanical materials. In some embodiments, the released substance is an active substance. In some embodiments, the substance is released from the source material by means of heating and/or airflow.

As used herein, the term "active substance" means a substance that comprises a compound having at least one medicinal and/or somatic and/or psychotropic effect.

A psychotropic effect optionally corresponds to a symptom that can be perceived by the patient. It is noted that in some cases a psychotropic effect may not be accurately perceived by the patient. Examples of psychotropic symptoms include, without limitation, paranoia, anxiety, panic attack, euphoria, pseudo-hallucinatory, sedation, conscious perception variation, joviality, metacognition and introspection, an enhanced recollection (episodic memory), amnesia, a sensuality variation, a variation in awareness of sensation and a variation in libido, dizziness, ataxia, euphoria, perceptual alterations, temporal distortion, intensification of ordinary sensory experiences, short term memory, and attention, impaired reaction, skilled activity, verbal fluency, dependence, melancholy and depression.

A somatic effect sometimes corresponds to a symptom which can be perceived by the patient or measured thereby. Examples for somatic symptoms include, without limitation, pain, migraine, nausea, dry mouth and a sensation of cold or hot hands and feet, increased heart rate, increased cerebral blood flow (e.g., migraine symptoms, "head pressure"), dilation of bronchial passages (e.g., coughing and difficulty breathing), dilation of blood vessels (e.g., shivers, skin redness, blushing), eye redness and pupil dilation, dry mouth, thirst, hunger or food craving.

In some embodiments, the compound includes one or more cannabinoids, for example Tetrahydrocannabinol (THC), Cannabidiol (CBD) and Cannabinol (CBN).

Optionally, the compound includes one or more alkaloids, for example nicotine and/or 1,2,3,4-Tetrahydroisoquinolines, Anabasine, Anatabine, Cotinine, Myosmine, Nicotrine, Norcotinine, and/or Nornicotine.

In some embodiments, the substance vaporizes at a temperature requiring a substantial exogenous heat input to reach a temperature above ambient temperature. For example, the substance vaporizes at a temperature within the range from 80° C.-250° C., or within another range having the same, higher, lower, intermediate and/or intermediate bounds, for example between 160-230° C. In some embodiments, the substance vaporizes at a temperature above 80° C., 100° C., 150° C., 200° C., 230° C., or another higher, lower, or intermediate temperature. In some embodiments, the time to reach a volatilizing temperature is, for example, about in a range between about 100 msec-5 sec, 100-750 msec, 150-300 msec, or another range having the same, larger, smaller, and/or intermediate bounds. In particular, the time is, for example, 250 msec or less, 500 msec or less, 1000 msec or less, or another greater, smaller, or intermediate value.

In some embodiments, the source material is distributed throughout a pallet comprising a carrier material. Optionally, the carrier material comprises at least one botanical substance, such as cannabis, tobacco, and/or other plant matter. Additionally or alternatively, the carrier material comprises a porous and air-permeable absorptive matrix; for example, a foam, sponge, felt, and/or another fiber matrix, which absorbs the active substance to fix it into place. In some embodiments, the absorptive matrix is substantially non-friable, providing sufficient strength, for example, to allow direct attachment of other cartridge components, such as a heating element, to or within the absorptive matrix without a requirement for additional mechanical support to preserve the integrity of the absorptive matrix surfaces and/or structure. In some embodiments, the pallet is friable; for example, comprising granules, fibers, or another fine structure compressed to form the pallet.

In some embodiments, the source material comprises one or more isolated materials, essential oils, extracted materials, and/or synthetic compounds.

According to some embodiments, the source material comprises plant material comprising at least one plant material selected from the group consisting of *Cannabis sativa, Cannabis indica, Cannabis ruderalis, Acacia* spp., *Conocybe cyanopus, Conocybe smithii, Copelandia bispora, Copelandia cambodgeniensis, Copelandia cyanescens, Copelandia tropicalis, Galerina steglichii, Gymnopilus aeruginosus, Gymnopilus luteofolius, Gymnopilus spectabilis, Gymnopilus purpuratus, Inocybe aeruginascens, Inocybe calamistrata, Inocybe corydalina* var. *erinaceomorpha, Inocybe haemacta, Panaeolus africanus, Panaeolus castaneifolius, Panaeolus subbalteatus, Pluteus salicinus, Psilocybe allenii, Psilocybe antioquensis, Psilocybe arcana, Psilocybe atlantis, Psilocybe aucklandii, Psilocybe australiana, Psilocybe aztecorum, Psilocybe azurescens, Psilocybe baeocystis, Psilocybe bohemica, Psilocybe brasiliensis, Psilocybe caerulescens, Psilocybe caerulipes, Psilocybe columbiana, Psilocybe cordispora, Psilocybe cubensis, Psilocybe cyanescens, Psilocybe cyanofibrillosa, Psilocybe fagicola, Psilocybe fimetaria, Psilocybe heimii, Psilocybe hispanica, Psilocybe hoogshagenii, Psilocybe liniformans* var. *americana, Psilocybe mexicana, Psilocybe moravica, Psilocybe natalensis, Psilocybe ovoideocystidiata, Psilocybe pelliculosa, Psilocybe portoricensis, Psilocybe quebecensis, Psilocybe samuiensis, Psilocybe sanctorum, Psilocybe semilanceata, Psilocybe semperviva, Psilocybe sierrae, Psilocybe silvatica, Psilocybe stuntzii, Psilocybe stuntzii* var. *tenuis, Psilocybe subaeruginosa, Psilocybe subcubensis, Psilocybe tampanensis, Psilocybe uxpanapensis, Psilocybe villarrealiae, Psilocybe weilii, Psilocybe xalapenensis, Psilocybe yungensis, Psilocybe zapotecorum, Amanita muscaria, Yage, Atropa belladonna, Areca catechu, Brugmansia* spp., *Brunfelsia latifolia, Desmanthus illinoensis, Banisteriopsis caapi, Trichocereus* spp., *Theobroma cacao, Capsicum* spp., *Cestrum* spp., *Erythroxylum coca, Solenostemon scutellarioides, Arundo donax, Coffea arabica, Datura* spp., *Desfontainia* spp., *Diplopterys cabrerana, Ephedra sinica, Claviceps purpurea, Paullinia cupana, Argyreia nervosa, Hyoscyamus niger, Tabernanthe iboga, Lagochilus inebriens, Justicia pectoralis, Sceletium tortuosum, Piper methysticum, Catha edulis, Mitragyna speciosa, Leonotis leonurus, Nymphaea* spp., *Nelumbo* spp., *Sophora secundiflora, Mucuna pruriens, Mandragora officinarum, Mimosa tenuiflora, Ipomoea violacea, Panaeolus* spp., *Myristica fragrans, Turbina corymbosa, Passiflora incarnata, Lophophora williamsii, Phalaris* spp., *Duboisia hopwoodii, Papaver somniferum, Psychotria viridis,* spp., *Salvia divinorum, Combretum quadrangulare, Trichocereus pachanoi, Heimia salicifolia, Stipa robusta, Solandra* spp., *Hypericum perforatum, Peganum harmala, Tabernaemontana* spp., *Camellia sinensis, Nicotiana tabacum, Nicotiana rustica, Virola theidora, Voacanga africana, Lactuca virosa, Artemisia absinthium, Ilex paraguariensis, Anadenanthera* spp., *Corynanthe yohimbe, Calea zacatechichi, Coffea* spp. (*Rubiaceae*), *Sapindaceae* spp., *Camellia* spp., *Malvaceae* spp., *Aquifoliaceae* spp., *Hoodia* spp. *Chamomilla recutita, Passiflora incarnate, Camellia sinensis, Mentha piperita, Mentha spicata, Rubus idaeus, Eucalyptus globulus, Lavandula officinalis, Thymus vulgaris, Melissa officinalis,* Tobacco, Aloe Vera, *Angelica,* Anise, Ayahuasca (*Banisteriopsis caapi*), Barberry, Black Horehound, Blue Lotus, Burdock, Camomille/Chamomile, Caraway, Cat's Claw, Clove, Comfrey, Corn Silk, Couch Grass, Damiana, Damiana, Dandelion, Ephedra, *Eucalyptus,* Evening Primrose, Fennel, Feverfew, Fringe Tree, Garlic, Ginger, Ginkgo, Ginseng, Goldenrod, Goldenseal, Gotu Kola, Green Tea, Guarana, Hawthorn, Hops, Horsetail, Hyssop, Kola Nut, Kratom, Lavender, Lemon Balm, Licorice, Lion's Tail (Wild Dagga), Maca Root, Marshmallow, Meadowsweet, Milk Thistle, Motherwort, Passion Flower, Passionflower, Peppermint, Prickly Poppy, Purslane, Raspberry Leaf, Red Poppy, Sage, Saw Palmetto, *Sida Cordifolia*, Sinicuichi (Mayan Sun Opener), Spearmint, Sweet Flag, Syrian Rue (*Peganum harmala*), Thyme, Turmeric, Valerian, Wild Yam, Wormwood, Yarrow, Yerba Mate, and Yohimbe. In some embodiments, the source material comprises one or more active substances extracted and/or isolated from one or more of the aforementioned plants and/or a synthetic version of such active substances.

In some embodiments, the source material comprises different plants, different strains, different blends, different additives, and/or different concentrations of one or more substances. It is noted that source material may comprise various forms, such as, for example, a solid bulk, solid particles, granulated particles, a solution or a powder.

In some embodiments, the source material comprises botanical substance which has maintained its microstructure intact.

In some embodiments, the source material vaporizes at a temperature requiring a substantial exogenous heat input to reach a temperature above ambient temperature. For example, the substance vaporizes at a temperature within the range from 80° C.–250° C., or within another range having the same, higher, lower, intermediate and/or intermediate bounds, for example between 160-230° C. In some embodiments, the substance vaporizes at a temperature above 80° C., 100° C., 150° C., 200° C., 230° C., or another higher, lower, or intermediate temperature.

Examples for source material constructs as described in PCT publication WO2016/001925 titled "DRUG DOSE CARTRIDGE FOR AN INHALER DEVICE" to Davidson and/or as described in PCT publication WO2016001921 titled "METHOD AND DEVICE FOR VAPORIZATION AND INHALATION OF ISOLATED SUBSTANCES" are incorporated herein by reference.

Figure 5:
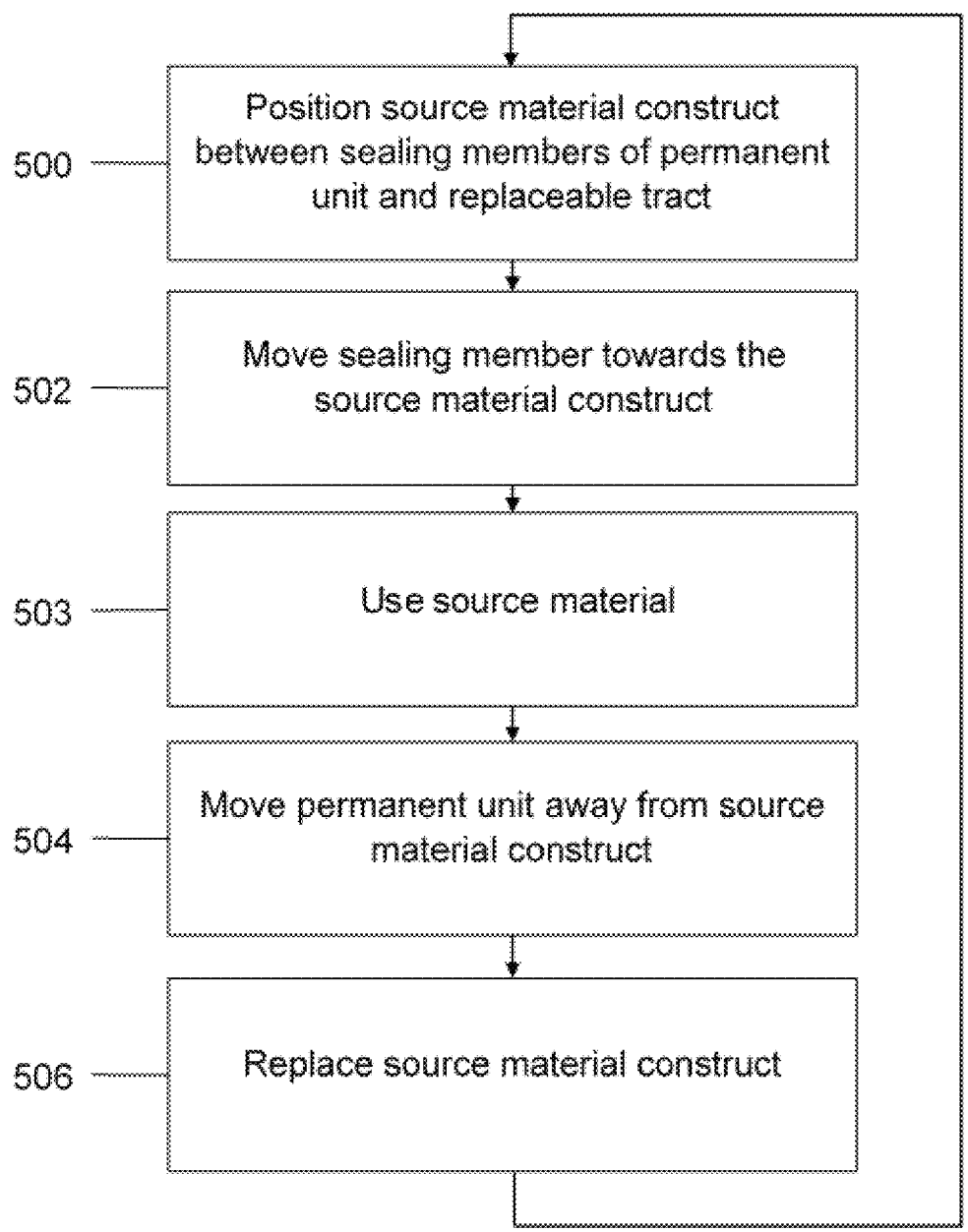

FIG. 5 is a flowchart describing mechanical operation of an inhaler device, according to some embodiments.

At 500, a source material construct is positioned in between two sealing members, a first sealing member forming a portion of the replaceable flow tract, and a second sealing member forming a portion of the permanent unit.

At 502, the permanent unit is moved towards the source material construct until the second sealing member presses the construct against the first sealing member.

In some embodiments, the applied pressure is strong enough to cause material of both sealing members to at least partially deform at the contact area between the sealing member and the construct, so that each of the sealing members adheres to an opposing surface of the construct, producing a sealed pathway that prevents air and/or vapors of active substance from escaping. Optionally, the degree of pressure is sensed using a sensor associated with the inhaler and/or with the replaceable flow tract. For example, this may be a pressure sensor or a pair of electrical contacts that come into contact with the construct and/or with any other portion associated with one or another flow tract thereby sensing the pressure and/or causing a mechanical hindrance to further motion.

At 503, once sealing is achieved, the source material in the construct that is currently in position is heated to allow delivery of the substance to the user.

Optionally, the source material is used only once. Alternatively, the source material is used a plurality of times. In some embodiments, distinct sections of the source material are used in any combination or order during one or more inhalations.

At 504, in accordance with some embodiments, following use of the source material in the construct that is currently in position, the permanent unit is retracted (504) away from the source material construct, and pressure is no longer applied onto the construct and onto the first sealing member. Optionally, the permanent unit is retracted to its initial position. Alternatively, the permanent unit is retracted a distance long enough to provide sufficient space for replacing of the construct. Alternatively, only the second sealing member is moved (for example rotated with respect to a long axis defined by the second conduit), to allow sufficient space for removal of the construct and insertion of a new construct into a use position.

At 506, the used construct is moved away from its position between the two sealing members and a new construct is placed instead of the used one. In some embodiments, replacement of the construct is carried out by a lever mechanism, a sliding mechanism, a pull arm, and/or other transport mechanism configured to move a used construct from the use position and replace it by a new construct. Transport mechanisms as described in PCT publication WO2016/001925 titled "DRUG DOSE CARTRIDGE FOR AN INHALER DEVICE" to Davidson are incorporated herein by reference.

It is noted that while movement of the permanent unit is described in this example, relative positioning of the replaceable flow tract, permanent unit and/or source material construct with respect to each other may be achieved by movement of any one or more of these components or portions thereof. For example, the construct can be "shoved" in-between sealing members (that are engaged or in close proximity one to the other); one or both of the sealing members can be moved towards and away from the other and/or towards or away from the construct; the replaceable flow tract can be moved towards the permanent unit to bring the sealing members into sealed communication; the construct can be rotated, advanced and/or otherwise re-positioned to locate a different source material section in a use position; an extendible portion of one or more of the components may be extended and/or other manners or combinations of relative movement of components forming the complete flow path.

In some embodiments, the new construct is obtained from a magazine or cartridge comprising a plurality of source material constructs. Additionally or alternatively, the new construct is obtained from a carousel arrangement of a plurality of cartridges, which can be rotated to replace a used construct by a new construct.

Additionally or alternatively, the source material is arranged in tape form, including for example an elongate layer of source material sandwiched between two electrically conductive, air-permeable layers, for example between electrically conductive mesh layers. Optionally, by pulling or rolling the tape, an unused tape section is advanced into position between the sealing members, replacing a used section of the tape.

In some embodiments, the used construct that was removed is reinserted into the cartridge. Alternatively, the used construct is moved to a dedicated compartment within the inhaler housing in which used constructs are collected. Optionally, the used constructs are disposed of.

In some embodiments, during replacement of the source material construct, the replaceable flow tract is not affected by the change and remains in position.

In some embodiments, the disposable flow tract is replaced between 1-15 times a month, for example between 1-3 times a month, between 1-5 times a month, between 4-8 times a month, between 10-15 times a month intermediate, larger or smaller number. Optionally, the flow tract is replaced according to a number of source material constructs used, for example replaced every 10-200 constructs, every 25-150 constructs, every 40-100 constructs, every 50-80 constructs or intermediate, larger or smaller amount. Additionally or alternatively, the flow tract is replaced periodically, for example every day, every 2-5 days, every 1 week or longer, every 3 weeks or longer, every 1 month or longer, every 3 months or longer or intermediate, longer or shorter time periods.

Figure 6:
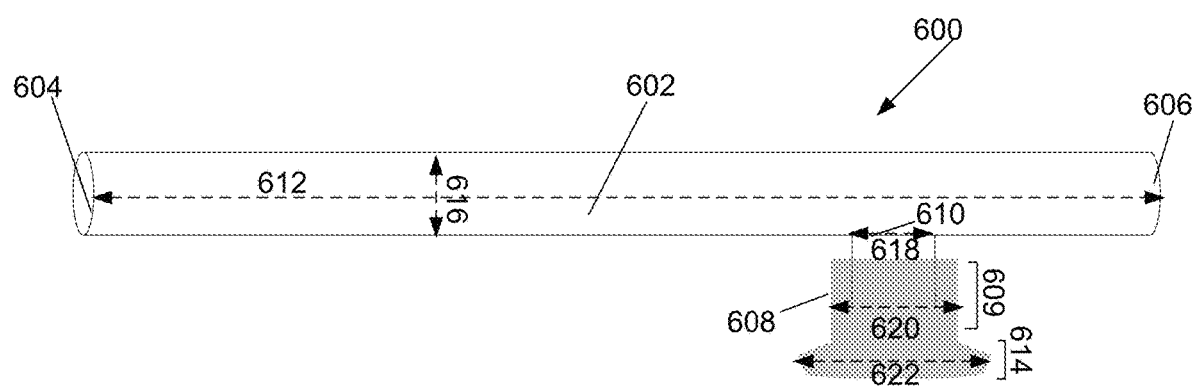

FIG. 6 schematically illustrates a T-shaped replaceable flow tract for use in an inhaler device, according to some embodiments.

In some embodiments, flow tract 600 comprises a conduit 602 including a first end 604 through which the vaporized active substance exits and is delivered to an inhaling user; a second end 606 through which ambient air may be allowed to flow into the conduit; and a sealing member 608 extending from a side opening 610 of the conduit (comprising a conduit portion to which sealing member 608 is attached).

In some embodiments, sealing member 608 is attached to a conduit portion which extends from opening 610 in a direction substantially perpendicular to a long axis 612 of the conduit. In some embodiments, sealing member 608 comprises a base portion 609 and ends with a widening 614 that defines a flexible lip. In use, when a source material construct is pressed against widening 614, the material of the sealing member is elastically deformed to adhere to the surface of the construct, so that the walls of the sealing member prevent the active substance imbued air from escaping.

In some embodiments, the sealing member comprises one or more materials rigid enough to prevent collapsing of the member when pressure is applied onto it from the direction of the construct, yet soft enough to allow deformation for fittingly engaging the construct. Such materials may include, for example, silicone.

In some embodiments, the sealing member comprises one or more heat-resistant materials suitable to withstand heating of the source material. Optionally, the materials are selected to remain stable at a maximal temperature of 100 degrees Celsius, 200 degrees Celsius, 250 degrees Celsius, 300 degrees Celsius or intermediate, higher or lower temperatures. Optionally the temperature is at least 30 degrees Celsius or at least 50 degrees Celsius higher than the vaporization temperature of the source material for which the inhaler device is intended.

Some examples for dimensions of the flow tract may include a conduit diameter 616 of between 4-6 mm or a cross section area of between 10 and 40 $mm^2$, a side opening cross section area 618 of between 20-40 $mm^2$ mm, a sealing member base cross sectional area 620 of between 40-60 $mm^2$, and a widening cross sectional area 622 of between 50-70 $mm^2$.

In some embodiments, a length of conduit 602 for example as measured between ends 604 and 606 of the conduit ranges between 2-15 cm, for example 4-8 cm or about 6 cm. In some embodiments, conduit 602 is long enough to provide for cooling of the vapors as they flow along the conduit until exiting from opening 604 to be delivered to the user. In some embodiments, cooling of the vapors is also provided by bypass flow entering the conduit through opening 606.

It is noted that the conduit and/or sealing member are not limited to a circular cross section any may be formed with other cross section profiles such, for example, rectangular, elliptic, triangular and/or others. A potential advantage of round cross section profiles (such as circular or elliptic) having no sharp edges or corners may include reducing condensation and build-up of residue along the flow tract.

In some embodiments sealing member 608 extends directly from opening 610 rather than from a short conduit extending from opening 610 to the base of the sealing member.

Figure 7A:
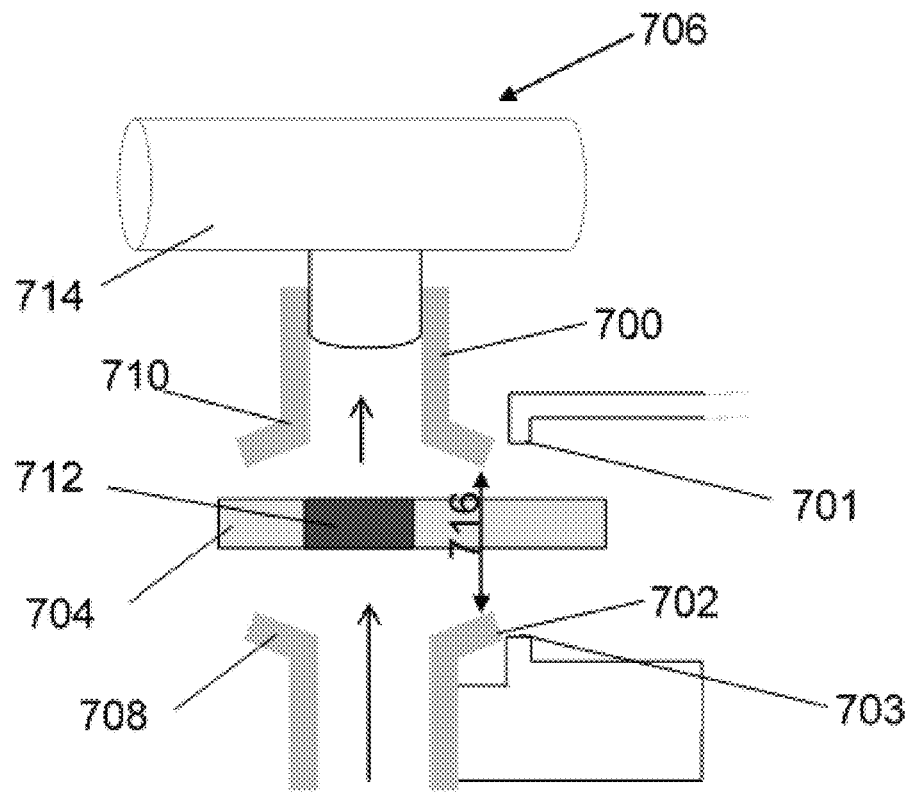
FIG. 7C illustrates another arrangement for clamping a source material construct between a replaceable flow tract and a permanent unit, according to some embodiments.
Figure 7B:
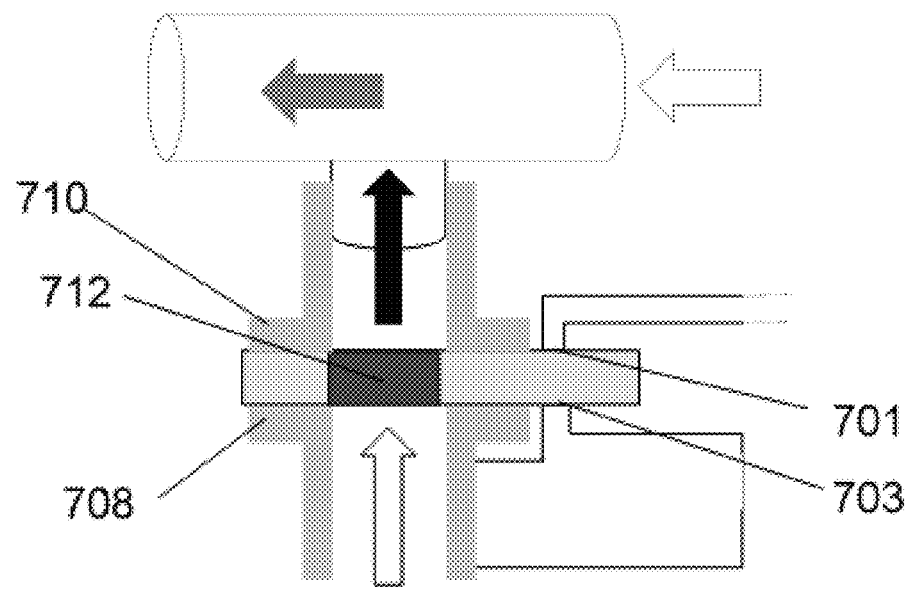

FIGS. 7A-B schematically illustrate coupling of a replaceable flow tract to a permanent unit of an inhaler device, according to some embodiments.

FIG. 7A illustrates first and second sealing members 700 and 702 in a spaced apart position from source material construct 704, according to some embodiments. First sealing member 700 extends from a T-shaped flow tract 706 towards the construct, while second sealing member 702 is positioned facing construct 704 from an opposite direction.

In some embodiments, as shown in the example of FIG. 7A, at the spaced apart position (which takes place for example when replacing a construct; at times there may be no construct between the sealing members) a minimal distance 716 exists between the opposing sealing members so that positioning of a construct in between the sealing members is not significantly interfered by the sealing members. Optionally, distance 716 ranges between, for example, 0.5-7 mm. Optionally the sealing members are closer to each other, or even in contact one with the other, and force is applied to insert a construct between them.

In some embodiments, in use, sealing member 702 is advanced towards construct 704 to a position in which a widening 708 of the sealing member is pushed against the construct, as shown in FIG. 7B. In turn, the construct is pushed against a widening 710 of the first sealing member, and a sealed flow path is set along an inner lumen defined by the sealing members and the intervening construct.

In some embodiments, the sealing members are aligned such that their openings are aligned with an opening or region 712 of the construct in which source material (or a portion of source material) is contained. Optionally, an aperture defined by each of the sealing members is shaped to overlap with opening 712 of the construct. Optionally, the widening portion of the sealing members is pliable enough so that when compressed the construct (or vice versa) a contact area of the sealing member with the surface of the construct enlarges.

In some embodiments, as shown for example in FIG. 7A, a first electrical contact 701 is positioned within the inhaler at a location adjacent the first sealing member 700 (when in position). A second electrical contact 703 is associated with the second sealing member 702. In some embodiments, as the second sealing member 702 is moved towards the first sealing member 700, electrical contact 703 moves along with it and comes to contact with the construct. Eventually, for example as shown in FIG. 7B, the construct, second sealing member 702 and second electrical contact 703 move further until the construct comes to contact with the first electrical contact 701. The electrical contacts may sense the degree of pressure between them and an electrically conductive portion of the construct, thereby serving as feedback on the degree of pressure between the sealing members. Optionally, sensing resistance through the contacts is used to define when sufficient sealing was achieved. In an example, if the degree of pressure (as indicated by the measured electrical resistance between the contacts) is lower than a threshold, movement of one or both of the sealing members is actuated to further push the sealing members against each other (and against the construct positioned therebetween). In an example, the magnitude of force applied by the sealing members onto each other is between 20-50N or between 30-40N.

In some embodiments, electrical current which actuates the motor is monitored, for example to determine when to stop moving the second and/or replaceable flow tract. Optionally, motor actuation is ceased when a predetermined force applied by the sealing rings onto each other has been reached. In some embodiments, resistance between the first and second electrical contacts (for example as described above) is assessed, for example to determine that contact between the sealing members and the construct has been achieved.

In some embodiments, optical sensors such as a photo interrupter are positioned in the replaceable and/or second flow tracts for verifying movement and/or for detecting malfunction.

Optionally, heating comprises conduction heating. In an example, the source material construct comprises ferromagnetic material (e.g. as part of a mesh and/or interspersed within the source material itself). In some embodiments, at least one conduction coil is used for heating the ferromagnetic material and thereby heating the source material. Optionally, a conduction coil is included in the replaceable flow tract, for example as a part of the sealing member of the replaceable flow tract. Additionally or alternatively, a conduction coil is included in the second flow tract, for example as part of the sealing member of the second flow tract.

In some embodiments, circuitry for heating the material within the source material construct passes through one or both of the sealing members. Optionally, in such configuration, heating and sealing are carried out (optionally simultaneously) by the sealing members.

In some embodiments, one or more of the sealing members may be integrated in the source material construct.

In use, as illustrated in FIG. 7B, ambient air flows to and through the second sealing member 702, to and through area 712 of the construct, passing through the heated source material, through the first sealing member 702 and into conduit 714 of the flow tract, where bypass flow and carrier flow may blend and flow in the direction of an output to the user (e.g. a mouthpiece).

In some embodiments, the two sealing members are not identical in structure. The sealing members may vary to an extent in which sealed communication is still provided when the construct is positioned in between.

Figure 7C:
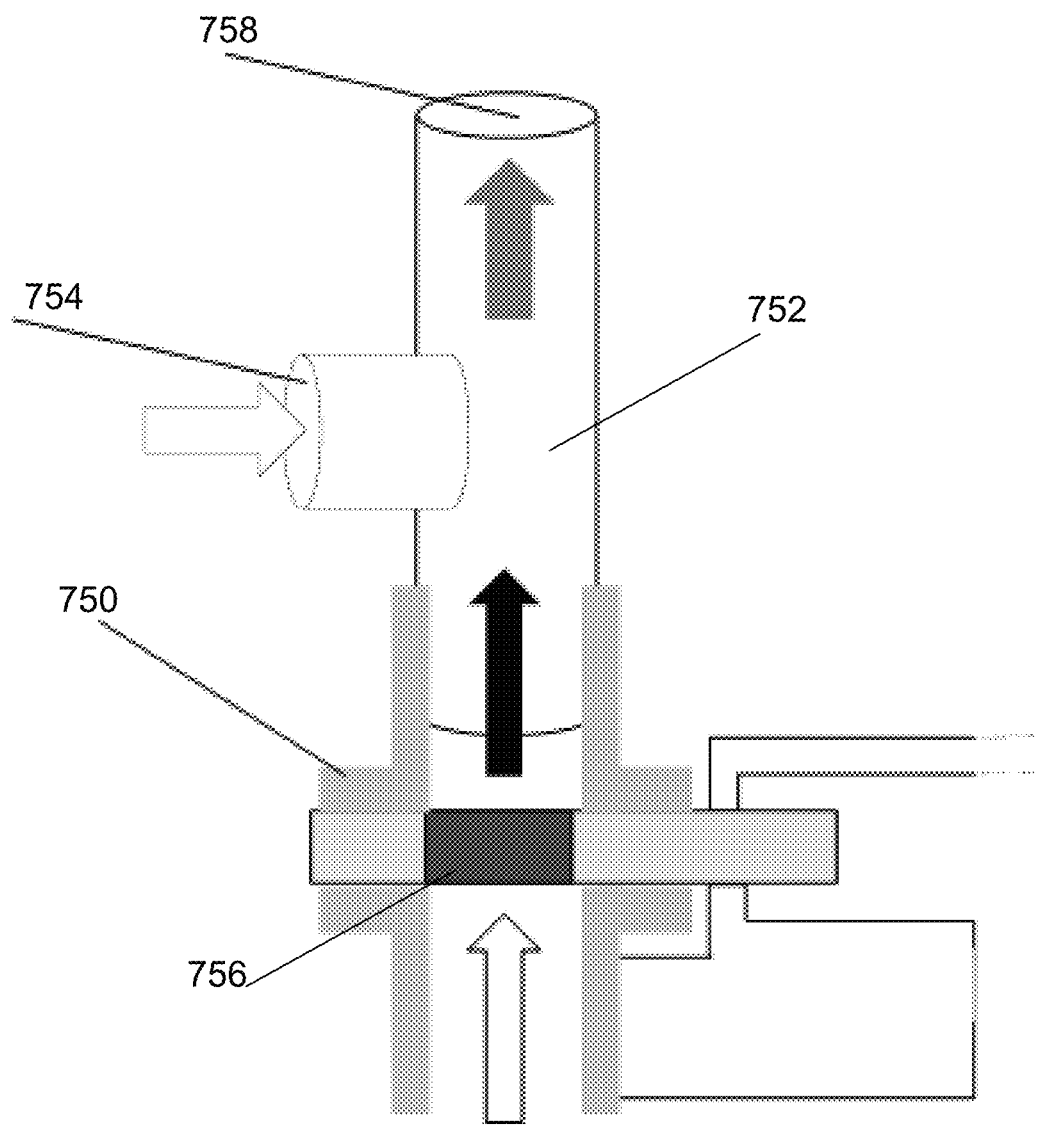

FIG. 7C illustrates another arrangement for clamping a source material construct between a replaceable flow tract and a permanent unit, according to some embodiments. This example is substantially as described in FIGS. 7A-B, except that sealing member 750 of the flow tract is aligned with respect to conduit 752 such that it is collinear with the conduit. In this example, bypass flow enters via conduit 754, optionally blending with carrier flow that passed through the source material construct 756 to flow towards an output 758 to the user.

Figure 8:
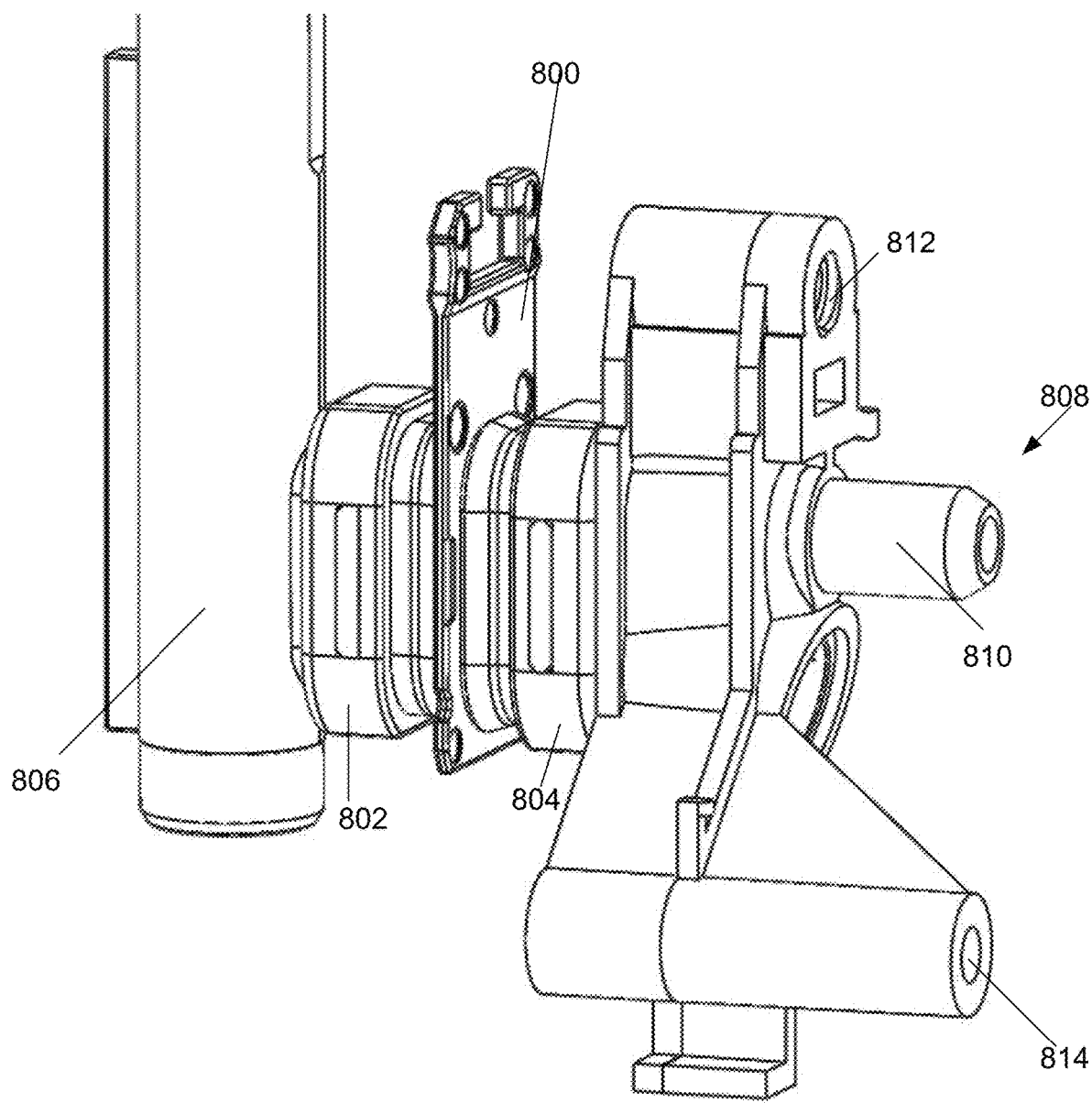
FIG. 8 illustrates clamping of a source material construct between a replaceable flow tract and a permanent unit, according to some embodiments.

FIG. 8 illustrates clamping of a source material construct between a replaceable flow tract and a permanent unit, according to some embodiments.

In the configuration shown herein, source material construct 800 is clamped between two sealing members 802 and 804, in accordance with some embodiments. In some embodiments, sealing member 802 is attached to a conduit that extends from a conduit 806 which in turn leads to the user. In some embodiments, sealing member 804 extends from a unit 808, the unit including a conduit 810 in fluid communication with the sealing member 804.

In some embodiments, unit 808 comprises a threaded channel 812 for receiving a screw. Optionally, advancement of unit 808 towards a position of the construct is carried out by threading the screw into channel 812, pushing unit 808 as a whole towards the construct. Optionally, retraction of unit 808 is obtained by unthreading the screw.

Other mechanisms may be used for moving unit 808 to and/or from the position of the construct. For example, unit 808 may be rotated on a hinge, lifted by a lever, and/or other mechanisms.

In some embodiments, unit 808 is slidably moveable over a lead pin (not shown herein), for example a lead pin received within passage 814.

FIGS. 9A-B illustrate a configuration as shown in FIG. 8, without the source material construct. FIG. 9B shows a cross section view of the described configuration. Once the construct is fitted in place and compressed, the inner lumens of conduit 810, sealing member 804, and sealing member 802 are in fluid communication with each other, defining a sealed pathway that passes through the source material. In operation, air is drawn into the inhaler device (optionally in response to inhalation of the user) entering the sealed pathway via conduit 810.

Optionally, bypass air enters via opening 814 of conduit 806, joining air imbued with the active substance that exited the sealed pathway at the juncture of sealing member 802 with conduit 806.

FIGS. 10A-B are an isometric view (FIG. 10A) and a cross section view (FIG. 10B) of a sealing member, according to some embodiments.

In some embodiments, sealing member 1000 comprises a base portion 1002 and a widening 1004.

In some embodiments, base portion 1002 is configured to be attached onto a conduit wall. In some embodiments, base portion comprises one or more slots 1006 for receiving connectors extending from the conduit. In this example the connectors are protrusions sized and shaped to tightly fit within slot 1006. Additionally or alternatively, the base portion is attached to the conduit by other fastening means, such as clips, pins, glue, and/or others. In some embodiments, the sealing member and conduit are manufactured as a single integral unit. Optionally, the sealing member and conduit are manufactured using over mold techniques, double injection techniques and/or others.

In some embodiments, widening 1004 extends from base portion 1002, increasing in cross sectional area towards an end of the sealing member that faces the source material construct position. In some embodiments, the walls of the sealing member at least at the widening are selected to be thick enough so that when the sealing member is pressed against the construct (or vice versa), due to the pliability of the material(s) from which the walls are formed, a contact area between the walls of the sealing member and the construct surface is enlarged, as the material at least partially deforms, "spreading" against the construct. The enlarged contact area may contribute for obtaining a tighter seal, and may be especially advantageous when the source material construct surface comprises a mesh, which sets a non-smooth surface due to indentations and protrusions set by the wire arrangement of the mesh.

In some embodiments, the widening defines an angle α of at least 15 degrees, at least 30 degrees, at least 50 degrees or intermediate, larger or smaller angles relative to a long axis 1012 defined by the inner lumen of the sealing member. A potential advantage of a sealing member including a widening, for example in comparison to a sealing member including a straight edge may include obtaining a tighter seal with the construct due to a contact surface area with the construct that gradually increases as the walls of the widening are pressed against the construct or vice versa.

In some embodiments, the sealing member dissipates at least some heat away from the source material construct. Optionally, by increasing a contact surface area between the sealing member and the construct, heat may be absorbed by the sealing member at a faster rate. This may assist in cooling of the source material construct, such as cooling of the heated mesh.

In some embodiments, widening 1004 is formed with an undercut 1014.

In some embodiments, base portion 1002 is thick enough to impart durability, as it used for attachment with the conduit (for example, the conduit is received within an opening 1018 defined by the base portion).

FIGS. 11A-B illustrate a replaceable flow tract 1100 structured to extend non-linearly with respect to an opening 1102 through which flow exits the inhaler to be delivered to the user. In some embodiments, conduit 1104 of the replaceable flow tract is formed with one or more curvatures such as horn-shaped curve 1106, extending to opening 1102. In some embodiments, sharp bends or corners along the flow tract are avoided, since they are prone to condensation more than soft-curves or straight arrangements.

In some embodiments, flow tract 1100 extends directly from opening 1102 in a substantially straight line such that it is linearly aligned with the opening.

In some embodiments, flow tract 1100 comprises a mouthpiece 1108, for example as shown in FIG. 11B. In some embodiments, a bottom surface 1110 of mouthpiece 1108 comprises and/or underlies one or more elements for aligning and/or coupling bottom surface 1110 of the mouthpiece with a surface of the inhaler housing (not shown) on which the mouthpiece is received. Such aligning and/or coupling elements may include, for example, one or more magnets 1112 positioned across respective magnets in the inhaler housing. Optionally, the magnetic attraction produced directs the mouthpiece into a position in which it is aligned with the inhaler housing. Optionally, the magnetic attraction produced is strong enough to hold the mouthpiece attached to the housing. Optionally, the magnetic attraction produced is at least strong enough to prevent unintentional pullout and/or rotation of the flow tract with respect to the inhaler housing. Additional and/or other aligning elements may include mechanical couplings such as pins, snaps, respective protrusions and recesses and/or others types of couplings.

Alternatively, in some embodiments, flow tract 1100 does not comprise a mouthpiece. Optionally, the flow tract is inserted through an existing mouthpiece of the inhaler device. Alternatively, a mouthpiece is separately received on the inhaler device, for example screwed onto, or otherwise attached to, conduit 1104.

Alternatively, an end portion of conduit 1104 extends outwardly with respect to the housing, forming a straw-like extension for engaging by the user's mouth.

In some embodiments, flow tract 1100 comprises a surface 1114 for example as shown in FIG. 11A which is mounted on top of a respective surface of the inhaler housing (not shown).

In some embodiments, flow tract 1100 comprises one or more protrusions and/or indentations and/or has an asymmetrical cross section for guiding insertion of the flow tract and/or for setting a locked orientation of the flow tract with the respect to the inhaler housing. In the example shown herein, flow tract 1100 comprises an elongated protrusion 1116, optionally rectangular, for guiding the flow tract during insertion into the inhaler housing, and a short protrusion 1118 located proximally with respect to the elongated protrusion for locking the flow tract in position and/or preventing unintentional pullout of the flow tract from the housing. Optionally one or more of protrusions 1116 and 1118 or any portion of flow tract 1100 may serve as a location indicator. The location feedback provided may be mechanical and/or electrical, and may serve as a prerequisite for operation. Optionally, the controller detects a current position and/or orientation of the flow tract according to a current position of the protrusions and/or according to contact formed by the one or more protrusions with other device portions, such as the housing.

As further described hereinabove, a sealing member 1120 is attached to a small conduit portion that extends from conduit 1104. Optionally, sealing member 1120 extends from a side opening of conduit 1104. In some embodiments, the side opening is closer to an opening 1124 from which air flow enters conduit 1104 than to opening 1102 from which air flow exits conduit 1104. For example, side opening 1120 may be located a distance of 2-20 mm or 10-15 mm from opening 1124 or any intermediate longer or shorter distance therefrom.

FIG. 12 is top view of an inhaler housing configured to receive a replaceable flow tract, according to some embodiments. In some embodiments, housing 1200 comprises a recess 1202 for receiving a replaceable flow tract. In some embodiments, recess 1202 comprises a portion 1204 shaped to receive a conduit of the flow tract, and/or a portion 1206 shaped for passage of a sealing member through and, in some embodiments, a portion 1208 in which an aligning protrusion and/or a positioning and/or a locking protrusion of the flow tract is inserted.

FIGS. 13A-F are examples of source material constructs and respective apertures of matching sealing members, according to some embodiments.

Figure 13:
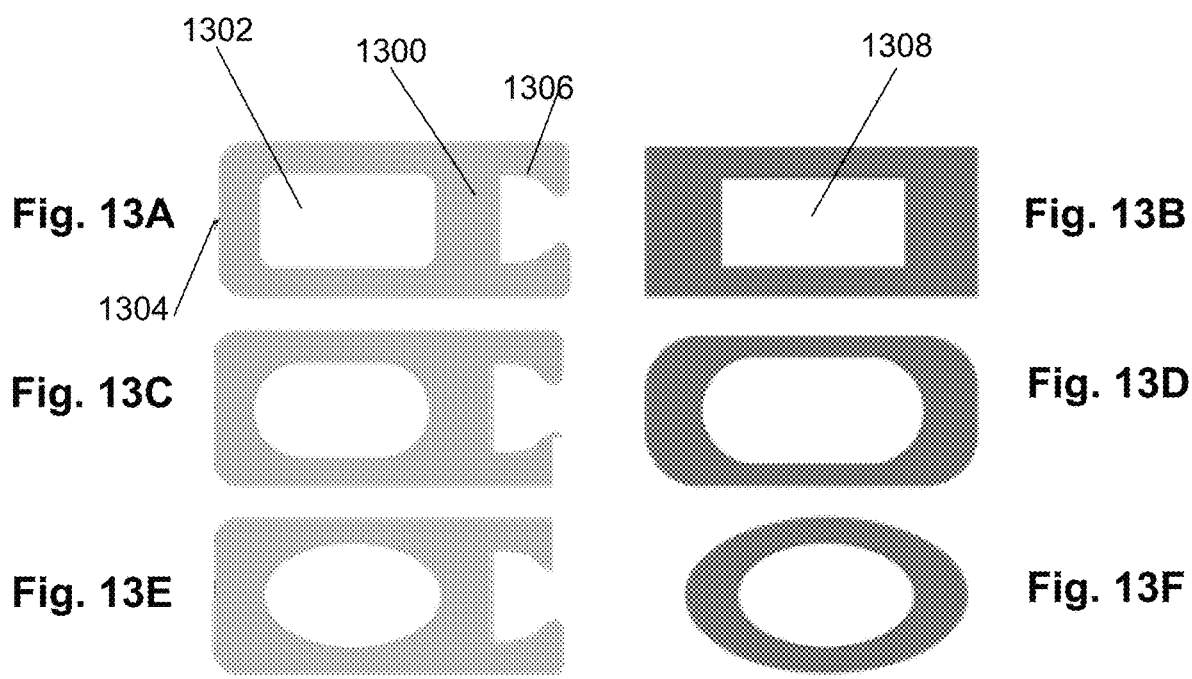

FIGS. 13A, 13C, 13E are examples of source material constructs, shown from a top view. In some embodiments, a construct comprises a frame 1300 defining at least one opening 1302 including source material, for example plant material.

In some embodiments, opening 1302 is shaped and/or sized so that the source material contained in the construct may be positioned in a path defined between the two sealing members, so that air flowing therethrough will carry substance(s) released from the source material when heated and carry those substances to and through the flow tract to the user.

In some embodiments, frame 1300 comprises one or more extensions 1306 by which the construct can be grasped or held, for example by a handle, lever and/or other element which transports the construct to a use position. In an example, a handle may pull a construct from a cartridge by obtaining hold of extensions 1306 and moving the construct into position, for example in between the two sealing members as described hereinabove.

In some embodiments, a mesh (not shown) and/or other air permeable layer extends at least across opening 1302. Optionally, a single mesh extends across opposite sides of opening 1302, extending for example along a top surface of the construct and then folding around an edge 1304 of the construct to extend along a bottom surface of the construct (opposite the surface shown herein).

FIGS. 13B, 13D, 13F show examples of sealing member apertures matching constructs 13A, 13C, 13E respectively. In some embodiments, an aperture 1308 of the sealing member is shaped and sized according to opening 1302 of the construct, so as to seal opening 1302 along its periphery. Optionally, the shape of aperture 1308 is different than that of opening 1302.

In some embodiments, opening 1302 and optionally its matching sealing member aperture 1308 are rounded (e.g. oval, as shown in FIGS. 13E and 13F) and/or comprise rounded edges (e.g. a rectangle comprising rounded corners, as shown in FIG. 13A). A potential advantage of a round profile may include a uniform heat distribution across the opening containing the source material, for example as compared to an opening formed with straight edges and/or sharp corners.

A potential advantage of a profile that does not include sharp corners (e.g. a rectangle having 90 degree angles) may include that the pressure needed for sealing the construct is lower than a pressure required for sealing sharp corner regions.

In some embodiments, a surface area of the sealing member that faces the construct is selected to be large enough so that an overlap between the sealing member and the construct when held against each other is sufficient to prevent flow from escaping from in between the surfaces. Optionally, the surface area contacted by the sealing member is selected to be large enough to dissipate heat away from the construct. In some embodiments, the sealing member contacting surface extends all the way to edge 1304 of the construct where the mesh bends so as to dissipate heat away from the near-bend area.

FIG. 14 illustrates a replaceable mouthpiece, according to some embodiments.

In some embodiments, mouthpiece 1400 comprises a conical outer surface 1402 tapering towards an opening 1404 through which flow exits the inhaler. In some embodiments, surface 1402 is sized to be placed in between a user's lips, resting against the lips.

In some embodiments, opening 1404 is centered with respect to a long axis 1406 of the mouthpiece. A potential advantage of a centralized opening may include directing flow towards a user's throat, for example as opposed to directing it towards the user's cheek. Optionally, opening 1404 is centered with respect to a long axis of the inhaler housing (not shown). Alternatively, opening 1404 is located a distance aside from the long axis.

In some embodiments, mouthpiece comprises more than one opening through which flow exits.

In some embodiments, mouthpiece 1400 forms an integral part of the replaceable flow tract. Alternatively, mouthpiece 1400 is separately attachable to the replaceable flow tract and/or to the inhaler housing.

FIGS. 15A-B show a source material construct 1500, according to some embodiments. In some embodiments, for example as described hereinabove, a mesh 1502 extends a surface of the construct, overlying opening 1504 in which the source material is contained. In some embodiments, mesh 1502 is U shaped and extends to an opposite side of the construct, bending along edge 1506. Alternatively, two or more mesh portions are mounted separately on the two opposing surfaces of the construct, extending across both sides of the opening 1504.

FIGS. 16C-H are various schematic layouts of replaceable flow tracts for use with an inhaler device, according to some embodiments, and FIGS. 16A-B are schematic layouts of inhaler devices, according to some embodiments, comprising replaceable flow tracts such as depicted in FIGS. 16C-H.

In some embodiments, for example as shown in FIG. 16F, a replaceable flow tract 1601 comprises a conduit 1600 open at one end 1602 and comprising a sealing member 1604 attached to a second opening of the conduit for example as described hereinabove at the other end. In some embodiments, when in use, airflow is allowed through conduit 1600, for example airflow may enter through sealing member 1604 and flow through conduit 1600 until exiting via opening 1602, such as to enter a mouth of the user.

FIG. 16G shows the replaceable flow tract of FIG. 16F, in which sealing member 1604 forms sealed communication with a source material construct 1606.

Optionally, the replaceable flow tract does not comprise an opening or path for bypass flow. Optionally, flow through the replaceable tract is limited only to flow that passed through the source material. FIG. 16H shows a replaceable flow tract essentially as shown in FIG. 16G engaging a second flow tract portion 1608.

Optionally, a sealing member 1610 of the second flow tract portion is positioned in sealed communication with source material construct 1606, for example being coupled to an opposite surface of the source material construct.

In some embodiments, for example as shown in FIG. 16C, the replaceable flow tract 1601 includes or is in fluid communication with a mouthpiece 1612. In some embodiments, a bypass flow path 1614 is defined through mouthpiece 1612.

Optionally, ambient air entering through opening 1616 formed in the mouthpiece passes through path 1614 and joins airflow imbued with at least one substance that is passing through the replaceable flow tract 1601, to exit the mouthpiece at opening 1618 to the user. FIG. 16D shows the replaceable flow tract of FIG. 16C in sealed communication with the source material construct; FIG. 16E shows the replaceable flow tract of FIG. 16C in sealed communication with the source material construct and with the replaceable flow tract.

In some embodiments, the replaceable flow tract, or any portion thereof, includes one or more structures (e.g. protrusions and/or cross sections and/or recesses) configured along the conduit, which correspond to respective shapes (e.g. recesses, cross sections or protrusions, respectively) in the inhaler housing (not shown).

Optionally, such structures may be used to guide the replaceable tract within the housing during insertions and/or extraction and/or to lock it in place so as to prevent unintentional removal.

Optionally, in operation, the source material construct is replaceable automatically by the device between uses. In some embodiments, the source material is positioned between two sealing members 1604 and 1610 within the inhaler device.

Optionally, the second flow tract portion 1608 is permanent within the device, and in some embodiments, in use, relative motion of the sealing members 1604 and 1610 causes them to form a sealed flow path through the source material construct.

FIG. 16B illustrates a layout in which a bypass flow path 1620 extends through a housing 1622 of the inhaler device, according to some embodiments.

Optionally, ambient air enters through opening 1624 of the housing and joins flow that passed through the source material at a juncture within the mouthpiece.

Additionally or alternatively, the juncture between the bypass flow path and the path in which air that passed through the source material flows is located at any other point between opening 1618 (inclusive) and sealing member 1604. FIG. 16A illustrates a layout which does include a bypass flow path.

Optionally, one or more valves (not shown) are used for controlling flow through one or more of the flow tracts, including replaceable flow tract 1601, second flow tract portion 1608 and/or bypass flow path 1620 (if included in the device).

In some embodiments, operation (e.g. a change in valve position) may be purely mechanical and a controller may not be used.

In some embodiments, insertion and/or removable of the replaceable flow tract to and from the inhaler device housing is for example as described in FIGS. 3A-C above.

The terms "comprises", "comprising", "includes", "including", "having" and their conjugates mean "including but not limited to".

The term "consisting of" means "including and limited to".

The terms "example", "exemplary" and "such as" are used herein to mean "serving as an example, instance or illustration".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An inhaler kit for delivery of at least one substance released from source material contained in a construct, the inhaler kit comprising:
    an inhaler housing comprising:
    a replaceable flow tract configured for extending between an output of the inhaler to a user and a location in which at least one substance is released from the source material; and
    a second flow tract positioned to direct ambient airflow to the location;
    the replaceable flow tract and second flow tract configured for being aligned with respect to each other so as to come into sealed communication with each other, the sealed communication formed at the location;
    wherein the replaceable flow tract comprises:
    a conduit comprising:
    a first opening;
    a second opening configured for being in fluid communication with a mouthpiece; and
    a third opening having an elastic sealing member extending therefrom, the elastic sealing member shaped and sized for pressing against the construct when the construct is within the inhaler housing.

2. The kit according to claim 1, wherein the third opening is configured along a wall of the conduit.

3. The kit according to claim 1, wherein the elastic sealing member is shaped to seal a coupling between a surface of the construct through which airflow passes and the conduit.

4. The kit according to claim 1, wherein the sealing member comprises a base portion extending from the third opening of the conduit, and a widening portion extending from the base portion, the widening portion ending with a pliable lip sized to engage the construct.

5. The kit according to claim 1, wherein the repleaceable flow tract comprises at least one protrusion extending from a wall of the conduit, the protrusion shaped and sized for at least one of guiding insertion of the repleaceable flow tract and for locking the replaceable flow tract to the inhaler housing.

6. The kit according to claim 1, wherein the replaceable flow tract comprises a mouthpiece defining an inclined surface tapering towards an opening, and the conduit extends to the mouthpiece such that flow existing the second opening exits the mouthpiece at the opening.

7. The kit according to claim 1, wherein the replaceable flow tract comprises one or more magnets for locking to the inhaler housing by magnetic attraction.

8. The kit according to claim 1, wherein the replaceable flow tract comprises one or more mechanical connectors for locking to the inhaler device.

9. The kit according to claim 1, wherein each of the replaceable flow tract and the second flow tract comprises a conduit including a sealing member, and wherein in use the second flow tract and replaceable flow tract are aligned with respect to each other such that apertures of the sealing members face each other.

10. The kit according to claim 1, comprising at least one replaceable flow tract provided separately from the inhaler housing.

11. The kit according to claim 1, wherein at least one of the replaceable flow tract and the second flow tract is configured to be moved with respect to the other flow tract or with respect to the location.

12. The inhaler kit according to claim 9, wherein the inhaler housing comprises a motor configured for actuating movement of at least a portion of the second flow tract that includes the sealing member relative to the location of substance release.

13. The inhaler kit according to claim 12, wherein the portion of the second flow tract is configured to be moved between a first position in which the sealing member contacts a source material construct when the construct is placed at the location, and a second position in which the sealing member is distanced from the location.

14. The inhaler kit according to claim 13, wherein an aperture defined by each of the sealing members is shaped according to an opening in the source material construct which exposes source material contained within the construct to the passage of air through.

15. The inhaler kit according to claim 1, wherein the housing comprises circuitry for activating a heating element associated with the source material construct when the construct is received at the location.

* * * * *